(12) United States Patent
Meibaum et al.

(10) Patent No.: US 9,220,827 B2
(45) Date of Patent: Dec. 29, 2015

(54) APPARATUS FOR EXTRACORPOREAL BLOOD TREATMENT

(75) Inventors: Joern Meibaum, Baunatal (DE); Stefan Moll, Melsungen (DE); Alex Castellarnau, Melsungen (DE)

(73) Assignee: B. BRAUN AVITUM AG, Melsungen (DE)

( * ) Notice: Subject to any disclaimer, the term of this patent is extended or adjusted under 35 U.S.C. 154(b) by 479 days.

(21) Appl. No.: 13/816,968

(22) PCT Filed: Aug. 17, 2011

(86) PCT No.: PCT/DE2011/001606
§ 371 (c)(1),
(2), (4) Date: May 24, 2013

(87) PCT Pub. No.: WO2012/022304
PCT Pub. Date: Feb. 23, 2012

(65) Prior Publication Data
US 2013/0237896 A1    Sep. 12, 2013

(30) Foreign Application Priority Data

Aug. 17, 2010 (DE) .......................... 10 2010 034 626

(51) Int. Cl.
*A61M 37/00* (2006.01)
*A61M 1/14* (2006.01)
(Continued)

(52) U.S. Cl.
CPC . *A61M 1/14* (2013.01); *A61M 1/16* (2013.01); *A61M 1/1609* (2014.02);
(Continued)

(58) Field of Classification Search
CPC ....... A61M 1/14; A61M 1/16; A61M 1/1603; A61M 1/1605; A61M 1/1607; A61M 1/1609; A61M 1/1613; G01J 3/0205; G01J 3/0208; G01J 3/021; G01N 21/33; G01N 2021/3185
See application file for complete search history.

(56) References Cited

U.S. PATENT DOCUMENTS

| 4,427,889 A | 1/1984 | Mueller |
| 5,772,606 A | 6/1998 | Ashibe et al. |
| 2004/0204634 A1 | 10/2004 | Womble et al. |

FOREIGN PATENT DOCUMENTS

| CN | 101161302 | 4/2008 |
| CN | 101801433 | 8/2010 |

(Continued)

OTHER PUBLICATIONS

CH 424 Instrumental Analysis Lab: Simultaneous Analysis of a Two-Component Mixture by UV-Vis; http://www.bama.ua.edu/~sstreet/Instrumental/uv-vis.PDF; Aug. 21, 2008, according to Internet Archive Wayback Machine.*

(Continued)

*Primary Examiner* — Philip R Wiest
*Assistant Examiner* — Ariana Zimbouski
(74) *Attorney, Agent, or Firm* — RatnerPrestia

(57) ABSTRACT

The invention describes an apparatus for extracorporeal blood treatment with a dialyzer which is separated by a semipermeable membrane in to a first and second chamber (29, 30), wherein the first chamber (29) is arrange in a dialysate pathway and the second chamber (30) is connectable to the blood circulation of a patient by means of a blood supply conduit (32) and a blood return conduit (31), an inlet (20) for fresh dialysate, an outlet (30) for spent dialysate, a measuring device (37) arranged in the outlet (36), wherein said measuring device (37) has at least one radiation source consisting of several light sources (1) for electromagnetic radiation. The invention is characterized in that the measuring device (37) is designed to generate substantially monochromatic electromagnetic radiation of different wavelengths, and to lead only one of these wavelength (at the same time) though the outlet (36) for spent dialysate, wherein at least one detector system (5) is provided for detection of the intensity or the absorption of the substantially monochromatic electromagnetic radiation passing through the outlet (36) for spent dialysate.

13 Claims, 5 Drawing Sheets

(51) Int. Cl.
*A61M 1/16* (2006.01)
*G01N 21/33* (2006.01)

(52) U.S. Cl.
CPC ............ *A61M 1/1613* (2014.02); *G01N 21/33* (2013.01); *A61M 2202/0498* (2013.01); *A61M 2205/3313* (2013.01)

(56) References Cited

FOREIGN PATENT DOCUMENTS

| DE | 29 34 190 | 3/1981 |
|---|---|---|
| DE | 69916053 | 3/2005 |
| EP | 1 083 948 | 3/2001 |
| EP | 2 005 982 | 12/2008 |
| JP | 02027264 | 1/1990 |
| JP | H11-76395 | 3/1999 |
| WO | WO98/55166 | 12/1998 |
| WO | WO 99/62574 | 12/1999 |

OTHER PUBLICATIONS

International Search Report for PCT/DE2011/001606 mailed Dec. 20, 2011.
Uhlin, "Haemodialysis Treatment monitored on-line by ultra violet absorbance" (Linkoeping University Medical Dissertation No. 962, 2006).
Vasilevsky et al., "Peculiar character of dialyzate ultraviolet extinction spectra as in indicator of nucleic acid metabolism in humans" (Journal of Biomedical Optics 10 (4), 44026, Jul./Aug. 2005).
Translation of the Notification of the First Office Action for CN 201180047850.1 issued Dec. 2, 2014.
Translation of CN Search Report for CN 201180047850.1.

\* cited by examiner

Absorption spectrum of malondialdehyde (c=1 mg/l)

Absorption spectrum of creatinine (c=1 mg/l)

APPARATUS FOR EXTRACORPOREAL BLOOD TREATMENT

CROSS REFERENCE TO RELATED APPLICATIONS

This application is the U.S. national phase application of PCT International Application No. PCT/DE2011/001606 filed Aug. 17, 2011, which claims priority to German Patent Application No. DE 10 2010 034 626.8 filed Aug. 17, 2010, the contents of each being incorporated by reference in their entirety.

FIELD OF THE INVENTION

The invention is related to an apparatus for extracorporeal blood treatment for differentiation of uremic toxins in the outflow of the apparatus.

BACKGROUND OF THE INVENTION

In patients with reduced or lost renal function waste products of the natural metabolism including uremic toxins are removed by means of renal replacement therapy or dialysis method. Thereby the removal of substances from the blood, which is taken from the patient and is led extracorporeal, is performed by contact of the blood with a dialysate, wherein blood and dialysate contact with each other not directly, but through a membrane. The dialysate is mixed with various salts and thus calls forth diffusive and convective effects which are responsible for the transport of substances from the blood into the dialysate via the extracorporeal arranged membrane. After performed removal of a portion of the waste substances the so treated blood is fed back to the patient.

For the test of a dialysis apparatus, parts of a dialysis apparatus or changed dialysis parameters, the concentrations of uremic toxin will be determined before and after a dialysis therapy. The reduction of the respective substances represents the central basis for the assessment of dialysis dose.

A common marker element is carbamide which is also known as urea. Accordingly, the urea reduction rate is regarded as a critical parameter in the dialysis technique. The determination of the urea reduction can be carried out in different ways.

A classical method represents the chemical determination of the urea concentration in the blood before and after a dialysis therapy. The problem of this method is, however, that the blood sample must be taken from the patient and be sent to a laboratory which is equipped for the determination of the urea concentration. This process can take quite several days.

Furthermore, the urea concentration or its change by the determination of the conductivity in the dialysate can be determined. A product on the market that works according to this principle is the product Biostat© Urea Monitor of the company Baxter. The problem during the measurement with conductivity is that conductivity change can be effected by other influence factors, e.g. by pH changes and that thus the measurement is distorted in circumstances.

A third possibility for determining the dialysis dose is the measurement of uric acid reduction which—as is generally known—corresponds substantially to the urea reduction, through a dialysis therapy by means of UV absorption measurements in the outflow of the dialysate. Uhlin has shown in his dissertation on the topic "Haemodialysis Treatment monitored on-line by ultra violet absorbance" [Linköping University Medical Dissertation No 962, 2006] that the absorption change in the outflowing dialysate at 280 nm represents a very good correlation to the concentration change of urea in the blood of the patient. Such a measuring device is described in EP 1 083 948 B1. In this prior art, both the configuration and the position of the sensor for dialysis technical applications is described.

Most of all, it is not possible with the apparatuses and methods known from the prior art to provide promptly on or during the therapy of the patient a differentiation of other waste substances or toxic substances of urea preferably simultaneously or at the same time.

DE 2934190 A1 discloses a method for molecular spectroscopy, in particular for the determination of metabolic products, in which the absorption of infrared radiation is measured though a sample containing a substance to be determined. As most preferred substance to be determined glucose is known. Thereby, the glucose determination is carried out in the whole blood or serum or in the urine with Raman lasers or carbon dioxide ($CO_2$) lasers as light source. DE 2934190 A1 describes that the concentration of several substances can be measured, wherein several wavelengths must be radiated simultaneously though the sample. In addition, DE 2934190 A1 points out the possibilities for developing an extracorporeal or also implantable artificial pancreas. The method described in DE 2934190 A1 shows the person skilled in the art that it is in principle possible to determine by means of infrared spectroscopy several substances simultaneously, i.e. their presence and allegedly, also their concentrations. This method is however unsuitable to measure blood samples or blood serum samples. Furthermore, the substances to be determined in the blood or dialysate flow indicate no clearly differentiable infrared spectrums. The substances measured in DE 2934190 A1 are well suitable to be determined by means of infrared. Due to the significantly different substance properties which are determined by means of infrared and UV, the measuring arrangement described in DE 2934190 A1 and the measuring methods cannot be applied to the UV range. In the UV range the absorption of the whole molecule, which is associated with the concentration of a substance, is determined, while certain types of bonds in a molecule are excited by means of IR and thus IR mainly is used to prove the presence of certain functional groups. The IR-measuring device described in DE 2934190 A1 cannot be simply replaced by a UV-measuring device or by a NMR-measuring device, because they are fundamentally different techniques, which are not equivalent interchangeable.

DE 69916053 T2 relates to a method for determining waste products in the dialysate during dialysis treatments. The method is for the exact determination of the amount of waste products in the dialysate during the dialysis treatment as well as for measuring urea or any other substance contained in the waste products. Thus, the determination can be optionally applied by measuring the substances which are most suitable for the selection of the dialyzer and the control of the dialysis machine in order to adjust the dialysis treatment to the patient. DE 69916053 T2 gives no evidence for the use of light emitting diodes (LEDs) and dispenses with a reference substance. Furthermore, DE 69916053 T2 gives the person skilled in the art no evidence, how several or all UV-active substances in the blood or the dialysate outflow can be determined quantitatively.

U.S. Pat. No. 5,772,606 discloses a urinal with a measuring system, with which the amounts of uric components, glucose, hemoglobin, albumin, lithium acetacetate, ascorbic acid, creatinine, sodium chloride and sodium nitrite can be determined. The measuring system disclosed in U.S. Pat. No. 5,772,606 uses the wavelength range between 400 and 2500 nm. As light source lasers are disclosed.

JP 02027264 A describes the measurement of proteins in the urine at a wavelength of 610 nm. As light source light emitting diodes (LED) are used. Proteins absorb, however also in the UV range below 210 nm and at 280 nm. However, the absorption at 280 nanometers requires the presence of the amino acids tryptophan and tyrosine in the amino acid sequence because other amino acids do not absorb in the UV range, wherein disulfide bonds and phenylalanine influence the UV absorption minimal. Below 210 nm absorb the peptide bonds in a protein. Due to the commonness of the peptide bonds in a protein, it is a very sensitive area of the protein spectrum. So a quantitative protein determination in sample liquids is possible, but using the obtained spectrum without knowledge of the respective extinction coefficient the proteins contained cannot be identified. Also with the apparatus disclosed in JP 02027264 A and the method, the determination of uremic toxins is not possible. The determination in the infrared range has the disadvantage that the sample to be measured is heated by the infrared radiation passing the sample. This can lead to rearrangement or degradation of the uremic toxins to be measured and to a change of the extinction coefficient so that with the inventive apparatus for extracorporeal blood treatment for differentiation of uremic toxins in the outflow of the apparatus the uremic toxins in the outflow of the apparatus can be no longer differentiated. Infrared measurements investigate other substance properties than UV measurements. The measuring methods are therefore to be considered substance-specific, as other optical properties are required. Thus, it is not possible with the experimental configuration described in JP 02027264 A to determine several or all UV active substances in the blood or the dialysate outflow. As above indicated, IR spectroscopy and UV spectroscopy are directed to clearly different molecular properties and both methods cannot be replaced equivalent.

SUMMARY OF THE INVENTION

Aspects of the present invention provide an apparatus for extracorporeal blood treatment for the quantitative and preferably for the qualitative and quantitative differentiation of uremic toxins in the outflow of the apparatus.

The inventors found surprisingly that contrary to the assumption in the prior art a qualitative as well as quantitative information of additional waste substances or toxic substances which are usually present in the spent dialysate in addition to urea, is possible in realtime or during the therapy of the patient, if at several wavelengths in the UV range the absorption of the spent dialysate is measured.

The uremic toxins are substances that are excreted in normal conditions of a healthy kidney, but retained in case of illness. The uremic toxins can influence biological functions negatively. Free water-soluble substances with low molecular weight (see Table 1) are differentiated from protein-bound substances (see Table 2).

TABLE 1

Free water-soluble substances in the blood plasma or blood serum. Modified from Vanholder et al. *Review on uremic toxins: classification, concentration and interindividual variability.* Kidney International. 2003;63:1934-1943.

| | | |
|---|---|---|
| 1-methyladenosine | erythritol | orotic acid |
| 1-methylguanosine | guanidine | oxalate |
| 1-methylinosine | guanidinoacetic acid | phenylacetylglutamine |
| asymmetrical dimethylarginine (ADMA) | guanidonosuccinic acid | pseudouridine |

TABLE 1-continued

Free water-soluble substances in the blood plasma or blood serum. Modified from Vanholder et al. *Review on uremic toxins: classification, concentration and interindividual variability.* Kidney International. 2003;63:1934-1943.

| | | |
|---|---|---|
| □-keto-□-guanidinovaleric acid | uric acid* | symmetrical dimethylarginine (SDMA) |
| □-N-acetylarginine | urea | sorbitol |
| arab(in)itol | hypoxanthine | taurocyamine |
| argininic acid | malondialdehyde* | threitol |
| benzylalcohol | mannitol | thymine |
| β-guanidinopropionic acid | methylguanidine | uracil |
| β-lipotropin | myoinositol | uridine |
| creatine | $N^2,N^2$-dimethylguanosine | xanthine |
| creatinine* | $N^4$-acetylcytidine | xanthosine |
| cytidine | $N^6$-methyladenosine | |
| dimethylglycine | $N^6$-threonyl-carbamoyladenosine | |

*Absorption in the UV range.

In addition to the free water-soluble substances there are protein-bound substances which are summarized in table 2.

TABLE 2

Protein-bound substances in the blood plasma or blood serum. Modified from Vanholder et al. (2003).

| | | |
|---|---|---|
| 2-methoxyresorcinol | indol-3-acetic acid | pentosidin |
| 3-deoxyglucosone | indoxyl sulfate* | phenol* |
| 3-carboxy-4-methyl-5-propyl-2-furanopropanonic acid (CMPF) | kinurenine | P—OH-hippuric acid |
| fructoselysine | leptin | putrescine |
| glyoxal | melatonin | quinolinic acid |
| hippuric acid* | methylglyoxal | retinol-binding protein* |
| homocysteine | $N^□$-(carboxymethyl)lysine | spermidine |
| hydroquinone | p-cresol* | spermine |

*Absorption in the UV range.

Further, substances with average molecular weight are the uremic toxins in the blood plasma or blood serum, such as adrenomedulline, atrial natriuretic peptide, cystatin, endothelin, and parathyroid hormone.

Table 3 shows finally an overview of uremic toxins, of which exact urine concentrations and/or uremic retention should be discussed and thus removed advantageously from the blood.

TABLE 3

Substances in blood plasma or blood serum, of which concentration and/or uremic retention is not ensured. Modified from Vanholder etal. (2003).

| | | |
|---|---|---|
| 1-alkyl-2-formyl-3,4-glycosyl-pyrrole | $β_2$-microglobulin-fragments* | $N^□$-carboxyethyllysine |
| 2-(2-fuoryl)-4(5)-(2-furanyl)-1H-imidazole | cadaverine | organic chloramine |
| 3-deoxyfructosone | crossline | oxidized low-density lipoprotein |
| 3-hydroxykinurenine | dimethylamine | parathyroid hormone fragments |
| 4-hydroxynonenal* | guanosine | pyrraline |
| advanced oxidation protein products (AOPP) | imidazolone | pyrrole aldehyde |
| advanced glycation end products-$β_2$-microglobulin anthranilic acid | methylamine | trimethylamine |

*Absorption in the UV range.

The uremic toxins detectable by means of UV absorption are marked in the tables 1 to 3 by the symbol "*". As uremic toxins to be determined are the UV active substances preferred creatinine, uric acid, hippuric acid, indoxyl sulfate, 4-hydroxynonenal, malondialdehyde, p-cresol, phenol, retinol-binding protein and β2-microglobulin-fragments and/or combinations thereof. "Detectable by means of UV absorption" means that the uremic toxin absorbs in the UV range, i.e. the uremic toxin is UV active and can therefore also be described as UV active uremic toxin.

It is an object of the invention to provide an apparatus that allows the determination of more than one UV active uremic toxin or all UV active uremic toxins during a dialysis session, or within a short time intervals or at the same time in the blood or the dialysate outflow in order to draw conclusions about the quality of the dialysis as well as the dialysis apparatus or specific components of the dialysis apparatus, which codetermine the removal of uremic toxins. The inventive apparatus and the inventive method can allow on the one hand during or promptly on the therapy of the patient at least a qualitative as well as quantitative information of a further waste substance or another toxic substance which is e.g. additional to urea in the spent dialysate. Furthermore, the inventive apparatus and the inventive method are used to make statement of the quality of a dialysis carried out and thus e.g. also of new membranes, filters, coatings, dialysates, dialyzers and dialysis machines and their possible advantageous properties in comparison to known embodiments.

The further waste substance or the further toxic substances or uremic toxins which are present in addition to uric acid in the spent dialysate, are preferably selected from the group comprising creatinine, malondialdehyde, indoxyl sulfate, and p-cresyl sulfate or p-cresol. Also combinations of the aforementioned substances are available. Preferred is a combination of uric acid, creatinine, and malondialdehyde. More preferred is a combination of uric acid, creatinine, malondialdehyde, indoxyl sulfate, and p-cresyl sulfate. Most preferred is a combination of the UV active uremic toxins comprising creatinine, uric acid, hippuric acid, indoxyl sulfate, 4-hydroxynonenal, malondialdehyde, p-cresol, phenol, retinol-binding protein and β2-microglobulin fragments.

This objective is actually solved by an apparatus with the features of claim 1. Advantageous embodiments of the invention are found in the dependent claims, the figures, the examples and the description.

The present invention is directed to an apparatus for extracorporeal blood treatment, which comprises or consists of following components:
  a dialyzer which is separated by a semipermeable membrane into a first and second chamber (29, 30), wherein the first chamber (29) is arranged in a dialysate pathway and the second chamber (30) is connectable to the blood circulation of a patient by means of a blood supply conduit (32) and a blood return conduit (31),
  an inlet (20) for fresh dialysate,
  an outlet (36) for spent dialysate,
  a measuring device (37) arranged in the outlet (36), wherein the measuring device (37) has a radiation source (1) for electromagnetic UV radiation,
  wherein the radiation source (1) consists of either at least two monochromatic light sources or at least one polychromatic light source with monochromators for generating monochromatic UV radiation,
  a microprocessor unit (14), a storage unit as well as an output unit (15), characterized in that the measuring device (37) is designed to generate substantially monochromatic electromagnetic UV-radiation of different wavelengths and to lead it through the outlet (36) for spent dialysate, wherein at least one detector system (5) is provided for the detection of the intensity or the absorption of the substantially monochromatic electromagnetic UV-radiation passing through the outlet (36) for spent dialysate and in the storage unit an equation system $$A_{\lambda i} = \sum_{j=1}^{n} A_j$$

is deposited, wherein $A_{\square i}$ is the total absorption of a mixture of substances at a predetermined wavelength $\square_i$, $A_j$ is the absorption of each substance within the mixture of substances and n is the number of the interesting components within the mixture of substances which contribute to the absorption.

If at least 2, preferably 5, more preferably 8, even more preferably 10, even more preferably 12, preferably 14, and preferably 16 monochromatic light sources such as LEDs are used, they are preferably individually controllable.

For the detection of the intensity or absorption at a specific wavelength only one wavelength is irradiated at one position through the dialysate outflow, i.e. the spent dialysate. Of course, inventively also simultaneously several absorption measurements could be carried out, wherein then at sufficiently separated and different positions monochromatic wavelengths are passed through the spent dialysate.

It is preferred that at one position on the dialysate outlet at a given time by means of a wavelength, i.e. a monochromatic UV radiation or a polychromatic radiation and corresponding filter or monochromators, the absorption of the spent dialysate is measured at a known temperature and through a known distance in order to determine inventively the concentration of the UV active uremic toxins in the spent dialysate.

Furthermore, the present invention is directed to a method for the determination of the concentration of UV active uremic toxins, wherein in the dialysate outlet the absorption of the spent dialysate is measured at a known temperature and through a known distance at specific wavelengths and at least as many measurements are carried out at different wavelengths, as UV active uremic toxins are contained in the spent dialysate and by means of an equation system $$A_{\lambda i} = \sum_{j=1}^{n} A_j,$$

wherein $A_{\square i}$ is the total absorption of a mixture of substances from UV active uremic toxins at a predetermined wavelength $\square_i$, $A_j$ is the absorption of a single UV active uremic toxin within the mixture of substances and n is the number of the interesting components within a mixture of substances which contribute to the absorption, and by this equation after the detection of the absorption at n characteristic measuring points the concentration of the n UV active uremic toxins in the mixture of substances is determined.

With the apparatus of the invention, it is possible to carry out a differentiation of preferably uric acid from other toxic substances or waste products in the dialysate of patient requiring dialysis, wherein the apparatus makes use of the optical UV spectroscopy and by which alternating or simultaneous measurements of the absorption of the spent dialysate at substantially different monochromatic wavelengths are possible. The apparatus of the invention allows in particular the determination of the concentration of all UV active uremic toxins present in the blood or in the spent dialysate, i.e. in the dialysate outflow. In the prior art still no dialysis machine is disclosed, which enable to determine quantitatively all UV active uremic toxins, namely creatinine, uric acid, hippuric acid, indoxyl sulfate, 4-hydroxynonenal, malondialdehyde, p-cresol, phenol, retinol-binding protein and β2-microglobulin fragments during a dialysis session, or within 30 minutes, preferably within 20 minutes, more preferably within 15 minutes, even more preferably within 10 minutes, even more preferably within 8 minutes, even more preferably within 7 minutes, even more preferably 6 minutes, and most preferably within 5 minutes. The UV measurement can be carried out simultaneously or at the same time, i.e. that is measured at least at 10 characteristic (definition of "characteristic" see below) wavelengths or measuring points simultaneously or successively or immediately successively.

The measurement of the previously known 10 UV active uremic toxins, however, does not require that no other UV-active substances should be present. On the contrary, the method of the invention will work still properly, if further UV active substances should be present in the blood or dialysate outflow, such as a drug which is UV active or a certain UV active component of the food which is taken up by the patient through the consumption of a large amount of a certain food and thus becomes detectable in the blood or dialysate outflow. While per UV active uremic toxin at least one UV-measurement is carried out at an appropriate measuring point, all 10 currently known UV active uremic toxins can be determined quantitatively or qualitatively and quantitatively. How the selection of suitable measuring point is performed will be described below in detail. The UV measurement can be carried out in the blood or dialysate outflow, while it can be measured in the dialysate outflow more precisely than in the blood, i.e. the concentration determination in the dialysate outflow can be carried out more precisely. Thereby it has to be considered that the concentration of the measured substance in the dialysate outflow must not necessarily be identical with the concentration of this substance in the blood, unless it is ensured that, for example, by a temporarily closed circuit, where the dialysate outflow is reintroduced into the dialyzer, the concentrations of the substances in dialysate outflow can adjust the concentrations in the blood.

The term "dialysate outflow" as used herein, refers to the spent dialysate, which exits after passing through the dialyzer as a waste product from the dialyzer. As used herein, the term "toxin" or "uremic toxins" refers to the herein disclosed UV active uremic toxins, namely, creatinine, uric acid, hippuric acid, indoxyl sulfate, 4-hydroxynonenal, malondialdehyde, p-cresol, phenol, retinol-binding protein and β2-microglobulin fragments.

Human beta-2-microglobulin is a serum protein which as full length protein consists of a singular polypeptide chain of 119 amino acids (GenBank accession number CAG33347 version CAG33347.1, GI: 48146249 dated Apr. 17, 2005). The molecular weight of human beta-2-microglobulin in full length is 11.6 kD. Fragments of human beta-2-microglobulin can be produced by enzymatic degradation of the human beta-2-microglobulin, wherein at least two fragments of the human beta-2-Microglobulins are produced. Each of the beta-2-microglobulin-fragments produced by enzymatic degradation consists of a polypeptide chain which comprises less than 119 amino acids of the human beta-2-microglobulin in full length.

To carry out the possibly precise measurements, the UV measurement is carried out at substantially monochromatic wavelengths or more simply, at monochromatic wavelengths. Substantially monochromatic wavelengths are characterized by a peak emission wavelength, by a dominant wavelength and a centroid wavelength, wherein the full width at half maximum (FWHM) is in the range between 10 and 25 nm. A decrease of the full width at half maximum thus leads to a narrower wavelength range for the peak emission wavelength. Generally, the full width at half maximum (FWHM), a function with a maximum means difference between the two argument values for which the function values are dropped to the half of the maximum. As light emitting diodes (LEDs), for example, LEDs from Hamamatsu or Laser Components or LEDs of other manufacturers with equivalent specifications can be used.

Absorption measurements in the spent dialysate at a wavelength of λ=280 nm has already been described in EP 1 083 948 B1. The sensor disclosed in EP 1 083 948 B1 could be used for the present invention. The novelty of the invention is that by the use of several individual substantially monochromatic wavelengths absorption measurements can be carried out. The applied wavelengths are characteristic in that in the spent dialysate, i.e. in the dialysate outflow preferably only the waste substances to be determined contribute to the absorption at these wavelengths, wherein these adsorptions could overlap at the measured wavelength, and could also overlap even with other UV active substances not to be determined. For the determination of the UV active uremic toxins it is imperative that wavelengths are used, which represent characteristic points of the spent dialysate. A characteristic measurement point of the spent dialysate should be understood that at this point of the spectrum, i.e, at this wavelength, the absorption substantially of the substance to be determined or several substances to be determined is determined. A characteristic point of the spectrum of the spent dialysate can be independent on, for example, local maxima, local minima and/or turning points, wherein at the characteristic wavelengths or measuring points either only one uremic toxin should determine the absorption, or in the overlapping of several UV active uremic toxins each toxin should significantly contribute to the total absorption at this wavelength, so that the proportion of each toxin to the total absorption can be determined at this wavelength as precisely as possible, wherein according to the equation systems disclosed herein the concentration can be calculated back. In addition, it will be measured advantageously at characteristic points, i.e. wavelengths, at which at most two or three or four substances overlap, i.e. absorb there, wherein the number of the characteristic points, i.e. wavelengths, correspond to at least the number of toxins to be determined, as otherwise the equation system cannot be solved. As characteristic wavelengths or measuring points, edge points are also suitable, which are between a maximum and a turning point, if there the overlapping toxins contribute significantly to absorption. As unsuitable can be regarded measuring points or wavelengths for measuring, where, for example, 8 toxins overlap and only 2 toxins each with 40% determine the total absorption and the remaining 20% are determined for largely same proportions of the 6 remaining toxins. Each of the six remaining toxins can be neglected in respect of the total absorption, wherein the neglect of all six remaining toxins would lead to an excessive error in respect of the two dominant toxins, and simultaneously the 6 remaining toxins individually contribute to the total absorption in a very little amount that the determination of their concentration is also afflicted with a too large error at this point. Such points are regarded as unsuitable or not characteristic, and should be avoided. Further, it should also be mentioned here that the method and the apparatus of the invention is not limited to the currently known maximal 10 uremic toxins, but basically any number, for example, further 5 or further 10 or further 15 or further 20 UV active substances, together with the 10 known uremic toxins can be determined quantitatively, if the UV spectra of the individual compounds of the further UV active substances and their extinction coefficients are known.

Such an apparatus of the invention can be realized by the use of several light sources with monochromatic radiation or a polychromatic light source with a controllable wavelength-selective element, wherein the determination of the absorption of uremic toxins is carried out at different wavelengths, and with the aid of the wavelength-dependent extinction coefficient $\epsilon_{\lambda,i}$ the concentrations of uremic toxins are calculated. In principle, always the absorption of the spent dialysate is measured, which consists of the sum of the absorption of each uremic toxin. Thereby, it is not sufficient, however, to know the absorption of each uremic toxin. In order to determine the concentration, the substance-specific extinction coefficient and the optical measuring distance must be known (Equation 1). Each UV active substance or UV active uremic toxin to be determined is an unknown of an equation so that per each UV active substance at least one UV-measurement must be carried out. For each UV active substance or UV active uremic toxin to be determined, an equation with one unknown is resulted, so that the measurement must be carried out at least at one wavelength in the UV range. In case of two UV active substances to be determined, an equation with two unknowns is resulted, so that the measurement must be carried out at least at two wavelengths in the UV range. In case of three UV active substances to be determined, an equation with three unknowns is resulted and one measurement at least at three wavelengths must be performed etc. Generally in case of n UV active substances to be determined an equation with n unknowns is resulted, so that the measurement must be carried out at least at n wavelengths in the UV range.

Monochromatic electromagnetic radiation can be understood as radiation with a defined wavelength. Monochromatic electromagnetic radiation can be generated from a light emitting diode (LED). Light emitting diodes (LEDs) are electronic semiconductor elements, which emit electromagnetic radiation in a limited spectral range by current flow in the forward direction. The electromagnetic radiation emitted is almost monochromatic. The wavelength can in accordance with the configuration of the light emitting diode be in the visible range of the spectrum, in the infrared range or respectively in the ultraviolet range. The radiation source for the apparatus of the invention consisting of several light sources for emission of monochromatic electromagnetic radiation should be designed for emission of electromagnetic radiation in the range from 1 nm to 750 nm. In particular, the radiation source consisting of several light sources must be designed for emission of electromagnetic radiation in the range of ultraviolet radiation from 180 nm to 380 nm. For the measurement of uremic toxins LEDs are preferred, which emit in the range of ultraviolet radiation from 180 nm to 380 nm, more preferably in the range of ultraviolet radiation from 180 nm to 320 nm. To detect all UV-active substances, the detectors must be sensitive enough, since some substances are in regard to their UV spectrum only slightly different from each other. In addition, the resolution of the measuring device must be sufficiently high.

In the use of light emitting diodes (LEDs) it is also advantageous that light emitting diodes are not thermal radiator and the heat produced by the generation of radiation can be removed, for example by cooling fins on the back side of the light emitting diodes.

Alternatively, the radiation source consisting of several light sources can be designed for generating polychromatic electromagnetic radiation. To generate the substantially monochromatic electromagnetic radiation in the range from 1 nm to 750 nm, preferably in the range from 170 nm to 380 nm, and more preferably 180 nm to 320 nm, corresponding monochromators are provided. In particular, optical filters passing only a specific wavelength or a band-pass filter with several pass ranges are provided. Radiation source consisting of several light sources for generating polychromatic electromagnetic radiation in the ultraviolet range of the spectrum are for example, mercury-vapor lamps or deuterium lamps. For the present invention, conventional mercury-vapor lamps and/or deuterium lamps, optical filters and band-pass filters with several pass ranges can be used. The adaptation of the conventional mercury-vapor lamps and/or deuterium lamps, optical filter and band-pass filters with several pass ranges for generating monochromatic electromagnetic radiation in the range from 1 nm to 750 nm, preferably in the range from 180 nm to 380 nm, and more preferably 190 nm to 320 nm to the absorption behavior of uremic toxins to be determined is within the skills of a person skilled in the art.

In the following, the theoretical backgrounds are described in detail.

The Absorption is given by the Lambert-Beer law as follows:

$$A_{\lambda_i} = \epsilon_{\lambda,i} \cdot l \cdot c \qquad (1)$$

wherein $A_{\lambda,i}$ is the absorption at a specific wavelength $\lambda_i$, $\epsilon_{\lambda,i}$ is the wavelength-dependent extinction coefficient, I is the optical path length and c is the respective concentration of a substance. Often the absorption cross-section is also spoken. This is by equation (1) the absorption normalized to the length $$\frac{A_{\lambda i}}{l} = \varepsilon_{\lambda i} \cdot c.$$

If a mixture of substances consists of several absorbent substances, so the absorption of the mixture of substances consists additively of the absorptions of the individual components for a constant wavelength $\lambda_i$:

$$A_{\lambda i} = \sum_{j=1}^{n} A_j \qquad (2)$$

In equation (2) $A_{\lambda,i}$ is the total absorption of a mixture of substances, $A_j$ is the absorption of a single substance within the mixture of substances and n is the number of the components within the mixture of substances which contribute to the absorption. j represents the running index of the mathematical sum-operation. The formulas (1) and (2) are only valid if the wavelength $\lambda_i$ is constant. With this system, the absorption spectrum of spent dialysate can be disassembled in an equation system of n equations at n different wavelengths in order to identify the concentration of n uremic toxins. This is possible only, if the spectra of the uremic toxins are known and the spectra of the uremic toxins are sufficient different from each other or the aforementioned characteristic measuring points exist, as it is in the case of the UV active uremic toxins. Selection Criteria for a Characteristic Measuring Point or a Characteristic Wavelength:

As a characteristic point of the spent dialysate it is firstly understood that at this point of the spectrum, i.e. at this wavelength, the absorption is substantially dominated by the substance to be determined. That is, preferably, the absorption is dominated at least to 90%, preferably at least to 94% and especially preferably at least to 96% by that toxin. A characteristic measuring point can also be found where in the UV spectrum of the pure toxin has a maximum, a turning point or an edge point located between a maximum and a turning point. Moreover, characteristic measuring points or characteristic wavelengths can be found at a local maximum, a local minimum, edge points and/or turning points of the total spectrum of the measured sample. A characteristic measuring point, i.e, a wavelength can be selected, for example, using local maxima, local minima and/or turning points of the spectra of the uremic toxins, if these are different between the uremic toxins to be determined. For the case that the local maxima, local minima and/or turning points of the spectra of the uremic toxins should be overlapped at a specific wavelength, a characteristic measuring point can be selected in other ranges of the spectra of the uremic toxins, for example, in ranges of the spectra of the uremic toxins with positive or negative slope. For the case that the substance to be determined absorbs at a characteristic point of the spectrum of the solution to be measured, i.e. at a specific wavelength, the absorption contribute to the equation system. In case that at a characteristic point of the spectrum of the solution to be measured, i.e. at a specific wavelength, none of the substances to be determined contribute to the absorption, then the absorption at this characteristic point, i.e. this wavelength, does not contribute to the solution of the equation system. It is preferred that at the characteristic points of the spectrum of the measuring solution, such as the blood or the dialysate outflow at least one substance to be determined absorbs. It is also possible to measure at characteristic points, i.e. wavelengths, at which up to two or three or four substances overlap, i.e. absorb there, wherein the number of the characteristic points, i.e. wavelengths is at least the number of the substances to be determined, because otherwise the equation system cannot be solved. Characteristic measuring points or characteristic wavelengths for the UV measurement are thus such measuring points and wavelengths, where either only one toxin causes or dominates the absorption or where two or more toxins overlap each other and the overlapping toxins contribute individually significantly to the total absorption at this wavelength, so that the individual contribution of each toxin at the measured wavelength can be determined relatively precisely and the concentration thereof can be calculated. Unfavorable, however, are measuring points and the wavelengths at which several UV active substances overlap each other, but none of these substances dominates the absorption and all UV active substances contribute individually only little to the total absorption. Thus, one wavelength for the UV measurement is quite suitable, even if there 10 UV active substances overlap each other if, for example, a substance contributes to 50% to the total absorption, a second substance contributes to 40% to the total absorption and the remaining 8 substances contribute only to 10% to the total absorption, because then these 8 substances can be neglected and the two dominant substances can still be measured relatively precisely. Further, it is essential for the selection of the characteristic measuring points and the characteristic wavelengths that at n concentrations to be determined and n measuring points no redundant information may be obtained, i.e. the UV measurement at one of the n wavelengths may not lead to a result or an information which has been already obtained from another of the n measurements. This is, for example, the case, if at two wavelengths the absorption is dominated significantly by the same toxin. That is, at the two wavelengths the concentration of the same toxin is determined and a redundant information is obtained, because two measuring points for the determination of the same toxin were required. Such redundant informations are advantageous in order to increase the accuracy of the method, however, require that by n toxins more than n measurements have to be carried out, because a redundant information shall only be obtained from a (n+1) measurement. If you have n toxins and n measurements with two redundant informations, this will cause that only the concentrations of n−2 toxin can be determined. To determine the concentrations of all n toxins in this case at least 2 more measurements are needed.

Assuming that the absorption spectrum of dialysis patients is substantially dominated at a specific wavelength by uric acid, the equation system is simplified and other UV active uremic toxins can be calculated by the absorption measurement at other wavelengths (see tables 1 to 3). This is illustrated by the drawings of FIGS. 1 and 2. FIG. 1 shows the typical dialysis spectrum of a patient requiring dialysis, while FIG. 2 shows the profile of the spectrum of uric acid at a concentration of 1 mg/l. It is evident that the dialysis spectrum in the range of 320 nm to 290 nm follows substantially the spectrum of uric acid. In the wavelength range below 290 nm, the spectra differ significantly from each other, so that it can be assumed that there are other substances other than uric acid of the mixture of dialysis substances involved in the absorption, while from about 290 nm only uric acid contributes to the absorption.

By the equations (1) and (2) equation systems can be established for different wavelengths, which describe the absorption of a mixture for different wavelengths. In connection with the calculation of the concentration of uric acid, which constitutes at $\lambda=290$ nm substantially the absorption in the total dialysate, the measurement of the absorption at, for example, $\lambda=266$ nm, allows determination of another toxic substance such as malondialdehyde, if the absorption depends substantially on uric acid and a second substance at the second wavelength. Similar to the example of malondialdehyde, other substances such as creatinine, which codetermines substantially the absorbance of the dialysate, can be determined by this method. Since creatinine has its absorption maximum at ca. $\lambda=235$ nm, it makes sense to determine the absorption of the dialysate at $\lambda=235$ nm. Also further substances that are mentioned in Tables 1 to 3 and codetermine substantially the absorption of the dialysate, can also be determined by this method.

From the spectrum of uric acid according to FIG. 2, the ratio of the absorption of uric acid can be determined at two predetermined wavelengths. This ratio of the uric acid absorption applies also to the absorption of uric acid in the spent dialysate. Consequently, a linear equation system having at least two components can be established, and it is possible to determine the concentration or the reduction of other uremic toxins except or beside uric acid, such as malondialdehyde. As it is assumed that uric acid will be almost always present in dialysate outflow, a measurement at $\lambda=290$ nm is almost always advisable.

Following equations describe the necessary calculations exemplary for the UV active uremic toxins uric acid and malondialdehyde:

$$A_{\lambda=290nm} \approx \epsilon_{uric\ acid, \lambda=290nm} \cdot l \cdot c_{uric\ acid} \tag{3}$$

wherein $A_{\lambda=290\ nm}$ (dialysate)=$A_{\lambda=290\ nm}$ (uric acid).
With equation 1 it is further valid $$A_{\lambda=290nm}(\text{uric acid})=\text{konst} \cdot A_{\lambda=266nm}(\text{uric acid}) \tag{3a},$$

wherein konst is the ratio of the absorption of uric acid at the wavelength 290 nm and 266 nm.

If the absorption is now measured at a wavelength of 266 nm, at which the absorption is substantially composed only of the two substances, uric acid and malondialdehyde, the absorbance of the dialysate at 266 nm is:

$$A_{\lambda=266nm}(\text{dialysate}) = A_{\lambda=266nm}(\text{uric acid}) + A_{\lambda=266nm}(\text{malondialdehyde})$$

or is generalized to:

$$A_{\lambda=266nm}(\text{dialysate}) = A_{\lambda=266nm}(\text{uric acid}) + A_{\lambda=266nm}(\text{substance\_x}) \quad (3b)$$

with Lambert-Beer the following equation is obtained:

$$\lambda_{\lambda=266nm}(\text{dialysate}) \approx \epsilon_{\text{uric acid},\lambda 260nm} \cdot l \cdot c_{\text{uric acid}} + \epsilon_{\text{substance\_x},\lambda 260nm} \cdot l \cdot c_{\text{sustance\_x}} \quad (4)$$

After combining equation 3a and equation 4 it follows:

$$A_{\lambda=266nm}(\text{dialysate}) = \frac{A_{\lambda=290nm}(\text{uric acid})}{konst} + a_{\text{substance\_x},\lambda 266nm}, \quad (4a)$$

$$= \frac{A_{\lambda=290nm}(\text{uric acid})}{konst} + \varepsilon_{\text{substance\_x},\lambda 266nm} \cdot l \cdot c_{\text{substance\_x}}$$

and thus $$c_{\text{substance\_x}} = \frac{A_{\lambda=290nm}(\text{uric acid})}{konst \cdot l \cdot \varepsilon_{\text{substance\_x},\lambda 266nm}} \quad (4b)$$

If the substance_x is known which, for example, contributes beside uric in a major part to the absorption at λ=266 nm, the absorption of the substance_x can be determined with the aid of equation 4a at 266 nm and subsequently by equation 4b the concentration of the substance_x can be determined. A pre-condition is that the corresponding extinction coefficient $\epsilon_{\text{substance\_x},\lambda 260nm}$ is known, which is a substance constant and therefore can be measured in the laboratory.

This example can also be used for several unknown substance concentrations, if the measurement of the absorption is carried out with several wavelengths. Generally, it is referred here to a linear equation system of arbitrary order. In the following, as one of the substances to be determined the reference substance is indicated with a preferred wavelength $\lambda_1$=290 nm:

$$A_{\lambda i}(\text{dialysate}) \approx \frac{A_{\lambda 1}(\text{reference substance})}{konst_i} + \sum_{j=2}^{n} \varepsilon_{j,\lambda_i} \cdot l \cdot c_j =$$

$$\frac{A_{\lambda 1}(\text{reference substance})}{konst_i} + \sum_{j=2}^{n} A_j$$

wherein $\lambda_1$ is the wavelength, at which the reference substance is substantially the only substance in the spent dialysate which contributes to the absorption, thus preferred 290 nm and $$konst_i = \frac{A_{\lambda 1}(\text{reference substance})}{A_{\lambda i}(\text{reference substance})} = \frac{\varepsilon_{\lambda 1}}{\varepsilon_{\lambda i}}$$

as well as j is the concerned substance, $c_j$ is the corresponding concentration of the substance j in the dialysate, $konst_i$ is a ratio of the absorption of the reference substance in its pure form at the reference wavelength $\lambda_1$ to the absorption of the reference substance in its pure form at the wavelength $\lambda_i$, derived from a reference absorption curve of the reference substance, and $A_j$ is the absorption of the substance j at the wavelength $\lambda_i$.

In the following example, uric acid is preferably given as one of the substances to be determined:

$$A_{\lambda i}(\text{dialysate}) \approx \frac{A_{\lambda 1}(\text{uric acid})}{konst_i} + \sum_{j=2}^{n} \varepsilon_{j,\lambda_i} \cdot l \cdot c_j = \quad (4c)$$

$$\frac{A_{\lambda 1}(\text{uric acid})}{konst_i} + \sum_{j=2}^{n} A_j$$

wherein $\lambda_1$ is the wavelength, at which uric acid is substantially the only substance in the spent dialysate which contributes to the absorption, thus preferably 290 nm and $$konst_i = \frac{A_{\lambda 1}(\text{uric acid})}{A_{\lambda i}(\text{uric acid})} = \frac{\varepsilon_{\lambda 1}}{\varepsilon_{\lambda i}}$$

as well as j is the concerned substance, $c_j$ is the corresponding concentration of the substance j in the dialysate and $A_j$ is the absorption of the substance j at the wavelength $\lambda_i$.

The reference substance is selected from the group comprising the UV active uremic toxins creatinine, uric acid, hippuric acid, indoxyl sulfate, 4-hydroxynonenal, malondialdehyde, p-cresol, phenol, retinol-binding protein and β2-microglobulin-fragments and/or combinations thereof. As reference substance uric acid is preferred. By the use of uric acid as reference substance, the equation system (4b) can be simplified. The abovementioned equation system (4b) can be simplified as the following equation system (4c), so that no longer any of the n equations involves n unknowns. Rather, the number of unknowns is reduced to n=1 for one equation, to n=2 unknowns for two equations, to n=3 unknowns for three equations, etc. By the selection of a reference substance, the equation system can be simplified and is easier to solve, if the extinction coefficient of the reference substance is known. The concentration of the reference substance can be known or unknown. With the equation system, it is possible to determine n unknown concentrations at a characteristic measuring point, i.e. a specific wavelength, if the ratios of the concentrations of the n uremic toxins at the characteristic measuring point, i.e. the specific wavelength, are known. For the selection of one or more characteristic measuring points, the criteria mentioned in the section of selection criteria for a characteristic measuring point must be applied.

By iterative approach, this system of equations can be solved, for example, by measuring first at the wavelength at which only uric acid absorbes in the spent dialysate and then changing to wavelengths at which in the spent dialysate (i.e. in the dialysate outflow) beside uric acid one further substance absorbs substantially, then at which two further substances and then up to n further substances absorb. Thus, without the direct measurement, the absorption of a substance in the spent dialysate and with knowledge of the extinction coefficient, even the concentration of this substance in the spent dialysate can be determined.

The iterative approach is however only a possibility, although a preferred possibility, to solve the above equation system, which begins with the measurement of a reference substance, i.e. a reference toxin at a characteristic wavelength, where this toxin contributes to the UV absorbance almost alone, or at least to 90%, preferably to 94% and most preferably to 96%. Another possibility to solve the equation system from n equations for n concentrations to be determined of n uremic toxins is the selection of characteristic measuring points, where several toxins determine together the absorption spectrum significantly. If, for example, two measurement points are selected, where the same two uremic toxins dominate the absorption significantly, i.e. both together contribute to the total absorption to at least 90%, preferably 94% and most preferably to 96%, two variations are considerable. If at wavelength a toxin x has the absorption m and at this wavelength the toxin y the absorption n (including the possibility that m=n) and at the second measuring point at the wavelength b toxin x has the absorption m/2 and the toxin y the absorption n/2, then the ratios of the absorptions of the toxins x and y at both measuring points, i.e. at both wavelengths are the same, so that no further information is obtained from the measurement at wavelength b, i.e. the equation system of 2 equations with 2 unknowns cannot be solved. However, if the toxin x has at wavelength a the absorption m and at this wavelength the toxin y the absorption n (including the possibility that m=n) and at the second measuring point at the wavelength b toxin x the absorption m/2 and the toxin y the absorption n/3, then the ratios of the absorption of the toxins x and y are different at both measuring points and the equation system from two equations with two unknowns can be solved and the concentrations of the toxins x and y can be determined. In the latter case, the measuring points are characteristic, i.e. the spectra of two toxins sufficiently different, so that at the further measuring points no redundant information is resulted.

Thus, for the determination of the concentrations of n toxins it is important that at n wavelengths, the absorption is measured without obtaining redundant informations. Thus, to solve always the solution of an equation system from n unknowns, i.e. n concentrations of n toxins, the measurement at n+z wavelengths is recommended, wherein z=1, 2, 3, 4, 5, 6, 7, 8, 9 or 10.

For the determination of the respective absorption as described above, Lambert-Beer is also applied:

$$A_{\lambda_i} = \log\left(\frac{I_{A,0,\lambda_i}}{I_{A,t,\lambda_i}}\right) = \varepsilon_{\lambda_i} \cdot l \cdot c(t) \quad (5)$$

wherein $A_{\lambda_i}$ is the absorption at a specific wavelength $\lambda_i$, $I_{A,0,\lambda_i}$ is the intensity at the absorption detector with a reference solution, and $I_{A,t,\lambda_i}$ is the intensity at the absorption detector during a dialysis therapy at the time t at a specific wavelength $\lambda_i$. As in equation (1) $\varepsilon_{\lambda_i}$ is the wavelength-dependent extinction coefficients, l is the optical path length, and c(t) is the respective concentration of a substance at the time t.

By the determination of the intensity $I_{A,0,\lambda_i}$ with a reference solution—ideally fresh dialysate, since a possible absorption is not caused by toxins—at the start of the dialysis therapy and with a continuous determination of the intensity $I_{A,t,\lambda_i}$ during the therapy, the absorption for a specific wavelength $\lambda_i$ at anytime can be determined.

Absorption of UV Active Uremic Toxins

As already mentioned above, uric acid is to be expected in almost all patients on dialysis in the dialysate outflow so that a measurement at $\lambda$=290 nm should advantageously be carried out in order to determine the uric acid concentration.

In order to determine the concentration of malondialdehyde a measurement at $\lambda$=266 nm is recommended.

In order to determine the concentration of creatinine a measurement at $\lambda$=235 nm is recommended.

Thus, the absorption measurements are carried out at the following wavelengths: $\lambda$=320 nm, $\lambda$=310 nm, $\lambda$=305 nm, $\lambda$=300 nm, $\lambda$=290 nm, $\lambda$=280 nm, $\lambda$=270 nm, $\lambda$=266 nm, $\lambda$=260 nm, $\lambda$=250 nm, $\lambda$=245 nm, $\lambda$=240, $\lambda$=235 nm, $\lambda$=230 nm and $\lambda$=220 nm. As toxins to be determined creatinine, uric acid, hippuric acid, indoxyl sulfate, 4-hydroxynonenal, malonaldehyde, p-cresol, phenol, retinol-binding protein and β2-microglobulin-fragments and/or combinations thereof are preferred.

Preferred measuring points are at the wavelengths $\lambda$=310 nm, $\lambda$=290 nm, $\lambda$=266 nm, $\lambda$=235 nm and $\lambda$=220 nm. More preferred wavelengths are $\lambda$=310 nm, $\lambda$=290 nm, $\lambda$=280 nm, $\lambda$=266 nm, $\lambda$=250 nm, $\lambda$=245 nm, $\lambda$=235 nm and $\lambda$=220 nm. Most preferred are the wavelengths $\lambda$=320 nm, $\lambda$=310 nm, $\lambda$=305 nm, $\lambda$=300 nm, $\lambda$=290 nm, $\lambda$=280 nm, $\lambda$=270 nm, $\lambda$=266 nm, $\lambda$=260 nm, $\lambda$=250 nm, $\lambda$=245 nm, $\lambda$=240 nm, $\lambda$=235 nm, $\lambda$=230 nm, $\lambda$=220 nm and $\lambda$=205 nm.

Per uremic toxin to be determined an absorption measurement is preferred at a characteristic measuring point, i.e. at a specific wavelength, where this uremic toxin has an absorption maximum or at least a high absorption or a good absorption with little overlap. For the determination of the concentration of, for example 10 toxins, an equation system with 10 variables is obtained, so that 10 measurements are required, wherein the 10 measurements should not lead to redundant informations and should be carried out at characteristic points in order to obtain precise measurements. For the selection of one or several characteristic measuring points the criteria mentioned in the section of selection criteria for a characteristic measuring point must be applied. Moreover, if possible, in the measured range only this uremic toxin should absorb. If there is not such a wavelength or such a wavelength range for a specific uremic toxin, then this uremic toxin is measured at an absorption maximum or a high absorption, where an overlap with the absorption of one or more other uremic toxins is present, if the one or the at least one of the several other uremic toxins, which also absorb in this range, have another measuring range or another wavelength with an absorption maximum, or a high absorption, which is not or only slightly overlapped by the absorption of other uremic toxins. Since overall n equations with n unknowns are to be solved, the person skilled in the art selects the measuring points so that this equation system can be solved in order to determine the concentrations of the n UV active uremic toxins. If one UV active toxin is to be determined, an equation with one unknown results so that the measurement must be carried out at least at one wavelength in the UV range. From two UV active toxins to be determined, an equation with two unknowns results so that the measurement must be carried out at least at two wavelengths in the UV range, wherein no redundant information should be obtained. From three UV active toxins to be determined an equation with three unknowns results and one measurement at least at three wavelengths etc. Generally from n UV active substances to be determined an equation with n unknowns results so that the measurement at least at n wavelengths in the UV range must be carried out and no redundant information should be obtained. For the selection of the wavelengths it is important that the spectra of the uremic toxins are known and the spectra of the uremic toxins differ sufficiently from each other. The selection of the measuring points can be made, for example, using local maxima, local minima, edge points and/or turning points of the spectra of the uremic toxins, if these should differentiate between the uremic toxins to be determined. In case the local maxima, local minima, edge points and/or turning points of the spectra of the uremic toxins should be overlapped at a specific wavelength, a characteristic measuring point can be selected in other ranges of the spectra of the uremic toxins, for example, in ranges of the spectra of the uremic toxins with positive or negative slope, especially between a maximum and a turning point. It is preferred that at the characteristic measuring points of the spectra of the spent dialysate at least one toxin to be determined absorbs. It is also possible to measure at characteristic measuring points, i.e. wavelengths at which up to two or three or four substances overlap, i.e. absorb there, wherein the number of the characteristic measuring points, i.e. wavelengths, is at least the number of the substances to be determined, since otherwise the equation system cannot be solved.

If it is measured at characteristic measuring points, i.e. wavelengths, at which up to two or three or four substances overlap, i.e. absorb there, the equation system can be simplified and more easily solved. Furthermore, there is also the advantage that less characteristic measuring points, i.e. up to two or three or four, mean less deviations in the absorptions by measuring error. For the case that two of uremic toxins should be determined, which absorb at two characteristic measuring points, the absorption of the two uremic toxins must differ sufficiently at two characteristic measuring points. The absorption of the two uremic toxins at two characteristic measuring points is then sufficiently different, if the ratio of the absorptions of the two uremic toxins at the first of the two characteristic measuring points is unequal to the ratio of the absorptions of the two uremic toxins at the second of the two characteristic measuring points. If the ratio of the absorptions of the two toxins at the first of the two characteristic measuring points is equal to the ratio of the absorptions of the two uremic toxins at the second of the two characteristic measuring points, the equation system can not be solved, because a redundant information is obtained. For the solution of the equation system another characteristic measuring point, i.e. another wavelength is required, where the ratio of the absorptions of the two uremic toxins at the another characteristic measuring point must be not equal to the ratio of the absorptions of the two uremic toxins at the second characteristic measuring point. For n uremic toxins to be determined, at least n characteristic measuring points, i.e. n wavelengths must be selected, where the ratio of the absorptions of the n uremic toxins to be determined at least at one characteristic measuring point, i.e. one of the n wavelengths, must be unequal to the ratio of the absorption of the uremic toxins at the other characteristic measuring points, i.e. other wavelengths. This means that at two of the n measuring points the ratio of the absorptions of the toxins absorbing at this measuring point should be not identical or almost identical and if possible, should have a clear difference.

The extinction coefficient is characteristic for a specific substance at a specific wavelength and depends on the one hand on the temperature and on the pH-value, on the other hand, depends also on the solvent, which can incur interactions with the absorbing molecules. The extinction coefficient of the UV active substances to be determined are known in the prior art and can be found in textbooks, for example, *Lange's Handbook of Chemistry* (14. Ausgabe, Hrsg. J. A. Dean, 1992. McGraw-Hill, Inc., New York), *Second Handbook of Chemistry and Physics* (56. Ausgabe, Hrsg. R. C. Weast, 1975. CRC Press, Cleveland) or *Third Practical Handbook of Biochemistry and Molecular Biology*, Hrsg. D. G. Fasman, 1992. CRC Press, Boston. The determination of the extinction coefficient by the person skilled in the art is also possible, since the determination of extinction coefficient is within the skills of the person skilled in the art.

Measuring Device (37) and Radiation Source (1)

The sensor described for the carrying out the measurements, which is also named herein measuring device or UV sensor (37), is similar to the measuring device described already in the EP 1 083 948 B1. The difference is that the light source (1) now consists of at least two monochromatic light sources or a polychromatic light source, which can be controlled individually by means of a wavelength-selective element (2).

Reference detector (6) and absorption detector (5) are characterized especially in that they can detect the whole spectrum in the UV range between 160 nm and 400 nm wavelength. A drawing of such a sensor is shown in FIG. 5.

In order to carry out the described calculations with such a sensor during a dialysis therapy, a method is necessary which controls the measurement of the optical properties of the spent dialysate. In addition, different technical contents must be implemented, which are described below.

The Absorption Measurements

At the start of dialysis therapy a calibration of the absorption and reference detectors—at least, however, with two—wavelengths is necessary. Therefore, the sensor (37) must be filled with a reference fluid and the signal at the absorption detector (5) must be determined. In order to obtain a signal as strong as possibly at the absorption detector, it is preferred to configure the amplifier circuit, which converts the signal at the optical detector into an electrical signal, so that the intensity at the absorption detector is during the calibration with fresh dialysate near the maximum of the electrical amplification, so that also the electrical signal is at maximum.

Alternatively, the intensity of the LED can be also varied for each wavelength. Preferably, the controlling of the LED should be selected so that the current through the LED is less than 50% of the maximum allowed current in order to keep the load of the LED low and thus prevent aging effects. This should be carried out in coordination with the adaptation of the electrical amplifier circuit for the absorption detector during the calibration.

The methods described above in connection with a dialysis therapy are to be carried out at the time of the preparation of a dialysis therapy. The preparation in a dialysis therapy is characterized in that the extracorporeal blood circuit is not connected to the patient, so that it is ensured that after the dialysate preparation which usually is done at the very beginning of the preparation, fresh dialysate is in the outflow of the dialysis machine, so that a calibration can be carried out.

In addition, the temperature of the dialysate should also be considered during the calibration of the electrical signals which are generated by the UV sensor in the outflow of the dialysis. Since the temperature of the dialysate represents a critical function within the dialysis, the temperature detection can be used in order to ensure the accuracy of the calibration. Therefore, it is necessary that the calibration is carried out only when the temperature of the dialysate is in a suitable range, generally at about 35 to 37° C. The corresponding dialysate temperature is ensured during the preparation of a dialysis therapy by the dialysis machine.

This should be carried out for each wavelength (but at least two) of the system separately. Since the intensity of the light source and the sensitivity of the absorption and reference detectors depends on the radiated wavelength, the signals from both detectors must be determined in the calibration for the reference fluid and be stored in a storage, on which the actual measurements can be accessed in the further process of the dialysis therapy at any time. During the actual measurement within a dialysis therapy at time t, the measured intensity $I_{A,t,\lambda i}$ is determined for a specific wavelength and by means of equation (5) is associated with the reference value $I_{A,0,\lambda i}$ determined already during the calibration. This is done individually for each wavelength—but for at least two wavelengths—of the light source. It should be noted that the inventive method is not for a therapeutic method or a diagnostic method on the human body, because from the values obtained, neither a therapy nor a diagnosis is derived. The detected data are used only for the protocol of the dialysis process such as the proper function of a pump in the dialysis machine can be monitored and replaced in accordance with a malfunction or failure, what has also no connection with a treatment or diagnosis on the human body. Moreover, the obtained data draw conclusions about the quality of the dialysis session as well as newly used components in the dialysis apparatus and their suitability in general as well as for a particular patient.

The measurement of the absorption in the dialysate for different wavelengths is done successively, wherein the measured intensity $I_{A,t,\lambda i}$ and the reference intensity $I_{A,0,0\lambda i}$ are connected by means of equation (5). The reference intensities $I_{A,0,\lambda i}$ have been already determined earlier in the calibration phase so that the calculation of the respective absorption $A_{\lambda i}$ for each wavelength is carried out individually. Furthermore, the results of the individual absorption measurements can be used in order to be connected by means of the linear equation system described in the equations (2) to (5).

Preferred, the measuring time for a wavelength per light emitting diode is in the range between 1 and 30 seconds. The change between the wavelengths for the light emitting diode is carried out in the milliseconds/seconds range and is depend on the manufacturer specifications for the respective light emitting diode.

For substantially monochromatic radiation sources consisting of several light sources a light emitting diode is required per wavelength. Preferably, the number of the LEDs per housing is in the range of 1 to 5, preferably in the range of 1 to 8, more preferably in the range from 1 to 10 and most preferably in the range of 1 to 16, wherein a higher number of light emitting diodes can be also used, provided that the housing sizes or the sizes of the LEDs allow this. Also, two or more housings with one or more light emitting diodes are applicable.

Each UV active uremic toxin to be determined is measured at a wavelength. If a combination of different substances should be determined, thus for instance a combination of uric acid, creatinine, and malondialdehyde, three wavelengths are necessary, as it is apparent from the equation system (2). Thereby, each substance to be determined is an unknown in the equation (2). To determine n unknowns, consequently n equations are required. This in turn leads to a new equation (2) for each wavelength at which the absorption of a substance should be determined.

The absorption measurement for the range between 180 and 320 nm is carried out at discrete wavelengths. Since the spectra of the substances to be determined are sufficiently different, just as many measuring points are required as substances to be determined are present. Thus, the absorption measurements are carried out at the following wavelengths: $\lambda=320$ nm, $\lambda=305$ nm, $\lambda=290$ nm, $\lambda=280$ nm, $\lambda=266$ nm, $\lambda=245$ nm, $\lambda=235$ nm and $\lambda=220$ nm, when up to eight substances should be determined, and at $\lambda=320$ nm, $\lambda=310$, $\lambda=305$ nm, $\lambda=300$ nm, $\lambda=290$ nm, $\lambda=280$ nm, $\lambda=270$ nm, $\lambda=266$ nm, $\lambda=260$ nm, $\lambda=250$ nm, $\lambda=245$ nm, $\lambda=240$, $\lambda=235$ nm, $\lambda=230$ nm, $\lambda=220$ nm and $\lambda=205$ nm, when up to 16 substances and preferably the 10 mentioned uremic toxins should be determined. The characteristic measuring points are selected according to the criteria mentioned in the section of selection criteria for a characteristic measuring point. Likewise, measurements can be carried out at a selection range of the abovementioned wavelengths. Measurements at other than the abovementioned wavelengths are also possible. For the selection of the wavelengths it is important that the spectra of the uremic toxins are known and the spectra of uremic toxins differ sufficient, exemplary, by different local maxima, local minima or turning points or the spectra of the uremic toxins differ at the local maxima, local minima or turning points. Moreover, the extinction coefficients of the uremic toxins must be known at this wavelength. The determination of the extinction coefficient of the uremic toxins is within the skill of a person skilled in the art or can be found in textbooks.

Each light emitting diode in the measuring device is controlled individually, i.e. light emitting diodes of wavelength at which currently no measurement is made, are turned off. Accordingly, the time of a measuring cycle is between 1 to 30 seconds for a wavelength, at which is measured. If measurements for two wavelengths are carried out, the measuring time is in the range between 2 and 60 seconds. The time of the measuring cycles is thereby dependent on the number of measuring points or wavelengths. With polychromatic radiation sources consisting of several light sources all required wavelengths are emitted simultaneously, wherein at least one detector is present. If only one singular detector is present, a tunable filter must be installed upstream of the detector, wherein the tunable filter must be controlled in a manner so that the tunable filter allows all required wavelengths to pass sequentially. In this case, the time of the measuring cycle is in the range between 10 seconds and 5 minutes. The time of the measuring cycle is thereby dependent upon how long the filter needs to switch between wavelengths back and forth. If two or more detectors with each different wavelength-selective elements are present, the time of a measuring cycle is in the range from one to thirty seconds. Preferred is a measuring device with three detectors, wherein each detector has a filter and the filter of the first detector allows only light of the wavelength $\lambda_1$ to pass, the filter of the second detector only light of the wavelength $\lambda_2$ and the filter of the third detector allows only light of the wavelength $\lambda_3$ to pass.

As tunable filter diffraction gratings or crystals can be used, in which the wavelength selection is determined by the angle of incidence. The abovementioned filters are micromechanically tunable by a stepper motor which rotates the crystal or the grid. Alternatively electronically tunable filters can be used, wherein the material properties can be manipulated through the application of voltage such that only light with a specific optical wavelength passes through the crystal, or the grid. In case a polychromatic radiation source consisting of several light sources with two or more detectors is applied, wherein each detector has a separate filter, standard filter such as conventional band-pass filter for the UV range can be used. Further embodiments of the filter are within the skill of the person skilled in the art.

A measuring device comprises or consists of a radiation source and at least one detector. The radiation source may be one or more polychromatic light sources. In the case that only a polychromatic light source is used, radiation source and the light source are identical. The radiation source may also consist of two or more polychromatic light sources. In polychromatic light sources appropriate filters are to be used in order to limit the spectrum to the wavelength to be measured. It is preferred, if the radiation source consists of several monochromatic light sources. Monochromatic light sources do not need filters. The monochromatic light sources should emit the desired wavelengths, i.e. the characteristic wavelength such as $\lambda=320$ nm, $\lambda=310$ nm, $\lambda=305$ nm, $\lambda=300$ nm, $\lambda=290$ nm, λ=280 nm, λ=270 nm, λ=266 nm, λ=260 nm, λ=250 nm, λ=245 nm, λ=240 nm, λ=235 nm, λ=230 nm, λ=220 nm and λ=205 nm (λ represents the wavelength).

If a singular radiation source is used, this must be designed as a polychromatic radiation source. In the case of a singular polychromatic radiation source with a singular light source and a detector, the filters must be designed as tunable filters. The measurements are carried out sequentially at different wavelengths, in particular at λ=320 nm, λ=310 nm, λ=305 nm, λ=300 nm, λ=290 nm, λ=280 nm, λ=270 nm, λ=266 nm, λ=260 nm, λ=250 nm, λ=245 nm, λ=240 nm, λ=235 nm, λ=230 nm, λ=220 nm and λ=205 nm. Preferred is an embodiment of the measuring device with a polychromatic radiation source with a singular light source and several detectors, wherein each detector is provided with a specific filter. In this case the measurement is carried out simultaneously for all wavelengths. More preferred is the embodiment of a substantially monochromatic radiation source consisting of several light sources with a detector, wherein two or more of such configured measuring devices are sequentially arranged in the outlet 36 of the spent dialysate. The measurements at the different wavelengths are performed substantially simultaneously. Most preferred is an embodiment of the measuring device with at least two substantially monochromatic light sources consisting of several light sources and a detector, wherein the measurements for the different wavelengths are carried out sequentially. Alternatively, the measurements for the different wavelengths can be carried out simultaneously, if at least two measuring devices are available, which are arranged sequentially at the outlet 36 leading the spent dialysate and each of the measuring device is configured with at least a substantially monochromatic radiation source consisting of a light source and a detector.

Preferred is a radiation source which consists of 10 monochromatic light sources for the absorption measurements at the wavelengths λ=320 nm, λ=305 nm, λ=290 nm, λ=280 nm, λ=266 nm, λ=245 nm, λ=240 nm, λ=235 nm, λ=230 nm and λ=220 nm. More preferably a radiation source, which consists of 12 monochromatic light sources for the absorption measurements at the wavelengths 320 nm, 305 nm, 300 nm, 290 nm, 280 nm, 266 nm, 260 nm, 250 nm, 245 nm, 240 nm, 235 nm and 220 nm or 320 nm, 305 nm, 300 nm, 290 nm, 280 nm, 266 nm, 250 nm, 245 nm, 240 nm, 235 nm, 230 nm and 220 nm. Still more preferably a radiation source, which consists of 16 monochromatic light sources for the absorption measurements at the wavelengths λ=320 nm, λ=310 nm, λ=305 nm, λ=300 nm, λ=290 nm, λ=280 nm, λ=270 nm, λ=266 nm, λ=260 nm, λ=250 nm, λ=245 nm, λ=240 nm, λ=235 nm. λ=230 nm, λ=220 nm and λ=205 nm.

The above-mentioned radiation sources are particularly suitable to measure the absorption of following uremic toxins and to determine their concentration: creatinine, uric acid, hippuric acid, indoxyl sulfate, 4-hydroxynonenal, malondialdehyde, p-cresol, phenol, retinol-binding protein and β2-microglobulin fragments.

If a polychromatic light source is used, then such filters are used that measurements are enabled at the above-mentioned 10, 12 or 16 wavelengths.

To ensure that measurements of the intensities over a long period can be performed, it must be ensured that the light source emits constantly the intensity set up in the calibration also during the dialysis therapy, which usually takes about four hours. In addition to the required current running through the LED also the intensity of the reference detector $I_{R,0,\lambda_i}$ is also deposited in a storage after completion of the calibration of a wavelength. During the measurement of the absorption of a specific wavelength $\lambda_t$ it is ensured that the intensity of the reference detector $I_{R,t,\lambda_i}$ at a given time t is identical or almost identical to the calibration value $I_{R,0,\lambda_i}$. If this is not the case, then the intensity of the light source must be adjusted accordingly. For this, a control of the intensity is carried out at the reference detector. Controlled variable here is the current radiated intensity of a wavelength of the light source, which is detected at the reference detector, $I_{R,t,\lambda_i}$. This represents also simultaneously the actual value of the control. Set value is the respective reference intensity at the same wavelength from the calibration: $I_{R,0,\lambda_i}$. Through the comparison of actual value and set value, a control algorithm can be implemented, which minimizes the control deviation $\Delta I = I_{R,0,\lambda_i} - I_{R,t,\lambda_i}$. This can be realized e.g. with a PI control element. Actuator of the control is thus the current through the light source, which influences the intensity of the light source directly (usually linear). Disturbance variables of the system which bring about the control deviation are, for example, temperature changes or aging processes of the light source. Only after adjustment of the actual value to the set value, the measurement of the intensity $I_{A,t,\lambda_i}$ at the absorption detector can be continued.

By the use of at least two wavelengths, it is also possible to carry out a plausibility test. This plausibility test serves several purposes. Firstly, by measuring the absorption at e.g. $\lambda_1=290$ nm and $\lambda_2=230$ nm the ratio $A_{\lambda 2}/A_{\lambda 1}$ can be formed. From FIG. 1 it is shown that the absorption $A_{\lambda 2}$ is typically much greater than $A_{\lambda 1}$ in patients requiring dialysis. By the formation of this ratio, the functional capability of the sensor can be checked. For example, if the ratio is $A_{\lambda 2}/A_{\lambda 1} < 2$, e.g. an error message can be sent to the dialysis machine, which signals the improper function of the sensor.

On the other hand, the absorption of different wavelengths $A_{\lambda_i}$ can be used in order to divide the patients dependent on parameters such as nutritional status, etc. into different groups. Vasilevsiky and Konoplyov pointed out in 2005 in their article "Peculiar character of dialyzate ultraviolet extinction spectra as in indicator of nucleic acid metabolism in humans" (Journal of Biomedical Optics 10 (4), 44026, July/August 2005) that patients differ partly widely from each other based on the absorption curve of the dialysate in dependence of the wavelength. From the described method, by the use of two wavelengths (for example $\lambda_1=290$ nm and $\lambda_2=260$ nm), the respective group of patients can be determined. Thus, one can distinguish patients whose ratio $A_{\lambda 1}/A_{\lambda 2}$ is approximately equal to 1 (cf. FIG. 1), is >1 (e.g. more than 1.2) or their ratio is <1 (e.g. less than 0.9). The information of the patient's status could possibly be an indicator of parameters such as nutritional status or morbidity/mortality.

For a more detailed description of the invention drawings are attached with corresponding references. Further objects, advantages, features and application possibilities of the present invention will be provided with the following description of the embodiment examples with the drawings and examples. All described and/or illustrated features form for themselves or in any meaningful combination of the subject matter of the present invention, also independent of their abstract in the claims and their references.

In the FIGS. 7 to 9, 1 represents always the light source, which is designed poly- or monochromatic in accordance with the respective embodiment, 2 represents always the monochromator, 3 represents always the beam splitter, 4 represents always the measuring distance, 5 represents always the optical detector which is designed narrow-banded or broad-banded in accordance with the respective embodiment, and 6 represents always the reference detector.

DETAILED DESCRIPTION OF THE PREFERRED EMBODIMENTS

Examples

Example 1

Figure 1:
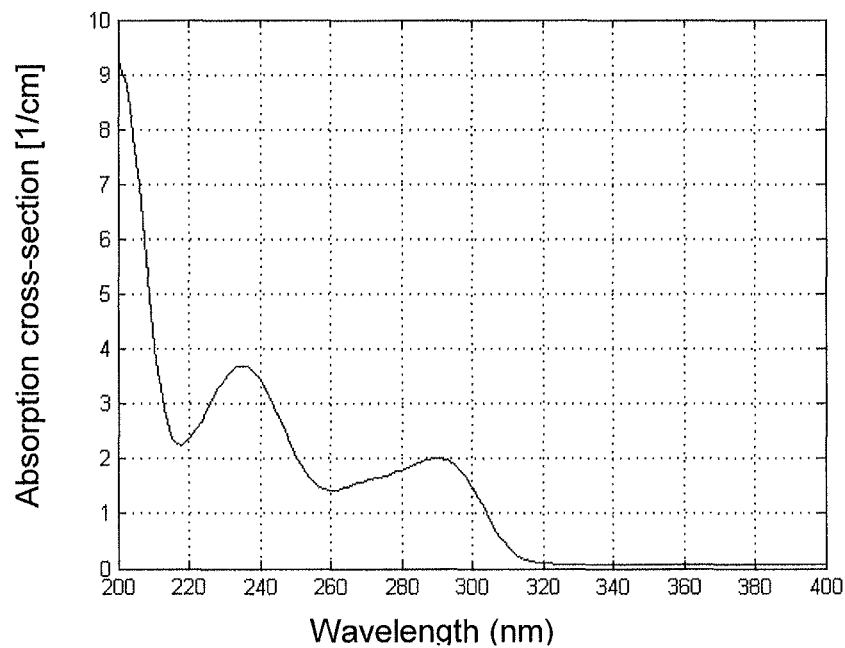
FIG. 1: Dependence of the normalized absorption of the irradiated wavelength for a typical dialysate spectrum of a patient requiring dialysis.

The dialysate sample of a patient requiring dialysis was taken 10 minutes after the start of treatment and its absorption in the wavelength range of 200 nm to 400 nm was determined spectrophotometrically. For wavelengths longer than $\lambda=340$ nm in this case the absorption is negligible. In the range of $\lambda=340$ nm to $\lambda=290$ nm, the absorption initially rises sharply, then behaves stably up to ca. $\lambda=260$ nm, in order to rise again sharply. At $\lambda=230$ nm a local maximum is seen. At wavelengths below $\lambda=220$ nm a further increase of the absorption was observed. Dialysate spectra of different patients differ usually in their intensity and the course of the absorption in the range between $\lambda=290$ nm to $\lambda=255$ nm. During the course remains almost constant in the displayed image in this range, at this point, also a local minimum (for example with $A_{\lambda=260\ nm}=0.5$) or a strictly increasing function (for example with $A_{\lambda=260\ nm}=1.5$) may exist. FIG. 1 shows the spectrum of dialysate sample from the dialysate outflow of the patient requiring dialysis.

Example 2

Figure 2:
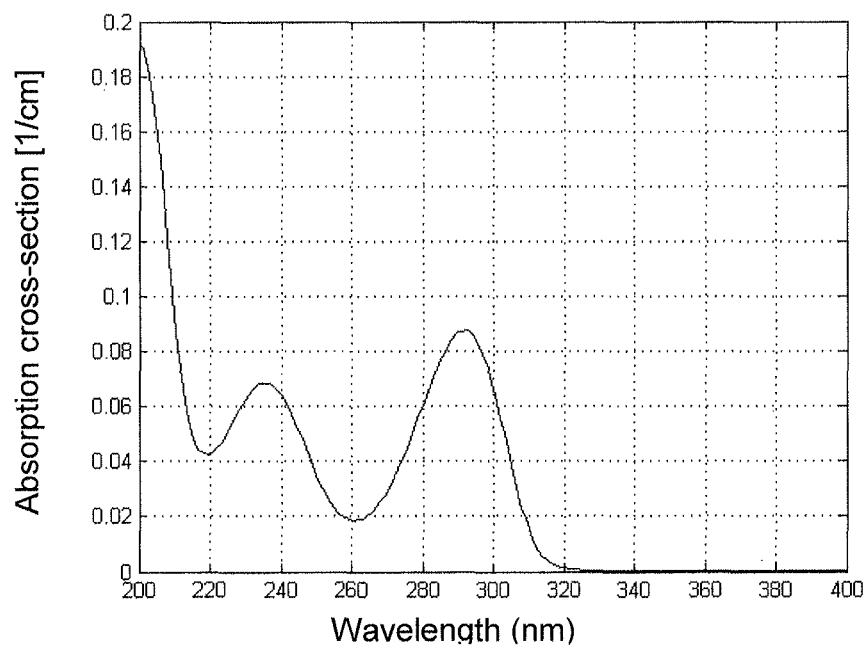
FIG. 2: Dependence of the normalized absorption of the irradiated wavelength for the small molecule substance uric acid.

The absorption behavior of uric acid at a concentration of c=1 mg/l was determined spectrophotometrically in water for the wavelength range of 200 nm to 400 nm. FIG. 2 describes the absorption behavior of uric acid in the range of $\lambda=400$ nm to $\lambda=200$ nm qualitatively. Clearly three local maxima at $\lambda=290$ nm, $\lambda=235$ nm and $\lambda=205$ nm are seen, wherein the maximum absorption is at the wavelengths of $\lambda=205$ nm and $\lambda=290$ nm ($A_{\lambda=205\ nm}=1.5$ or $A_{\lambda=290\ nm}=0.7$).

Example 3

Figure 3:
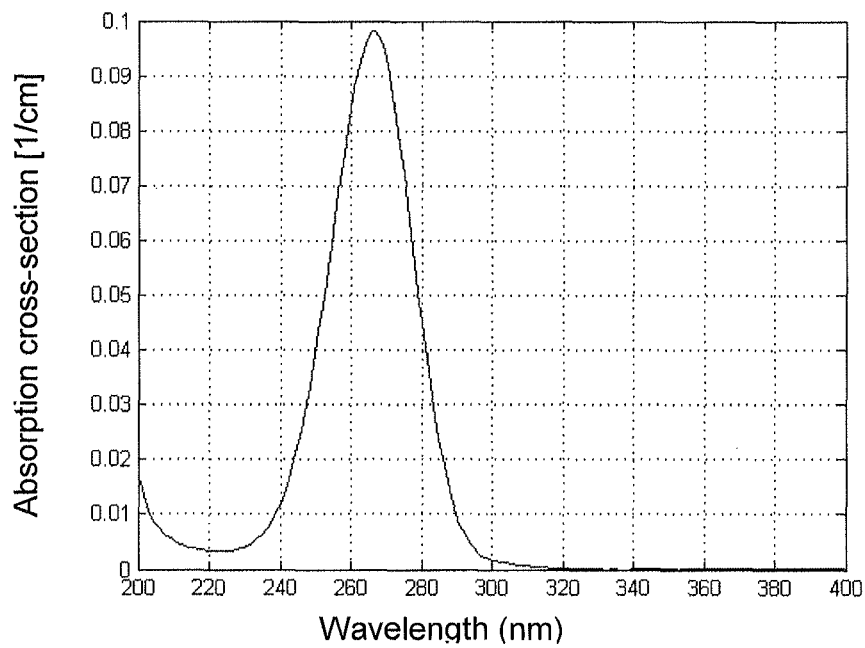
FIG. 3: Dependence of the normalized absorption of the irradiated wavelength for the small molecule substance malondialdehyde.

The absorption behavior of malondialdehyde at a concentration of c=1 mg/l was determined spectrophotometrically in water for the wavelength range of 200 nm to 400 nm. FIG. 3 describes the absorption behavior of malondialdehyde in the range of $\lambda=400$ nm to $\lambda=200$ nm qualitatively. Clearly a local maxima at $\lambda=266$ nm ($A_{\lambda=266\ nm}=1.005$) is seen

Example 4

Figure 4:
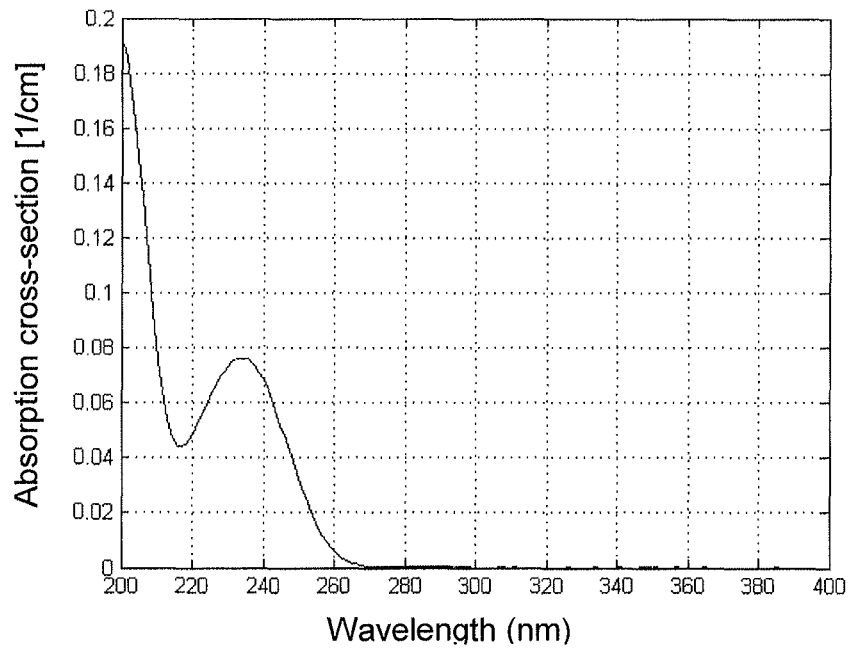
FIG. 4: Dependence of the absorption of the irradiated wavelength for the small molecule substance creatinine.

The absorption behavior of creatinine at a concentration of c=1 mg/l was determined spectrophotometrically in water for the wavelength range of 200 nm to 400 nm. FIG. 4 describes the absorption behavior of creatinine in the range of $\lambda=400$ nm to $\lambda=200$ nm qualitatively. Clearly two local maxima at $\lambda=205$ nm and $\lambda=235$ nm ($\lambda=0.19$ or $\lambda=0.076$) are seen.

Example 5

Figure 5:
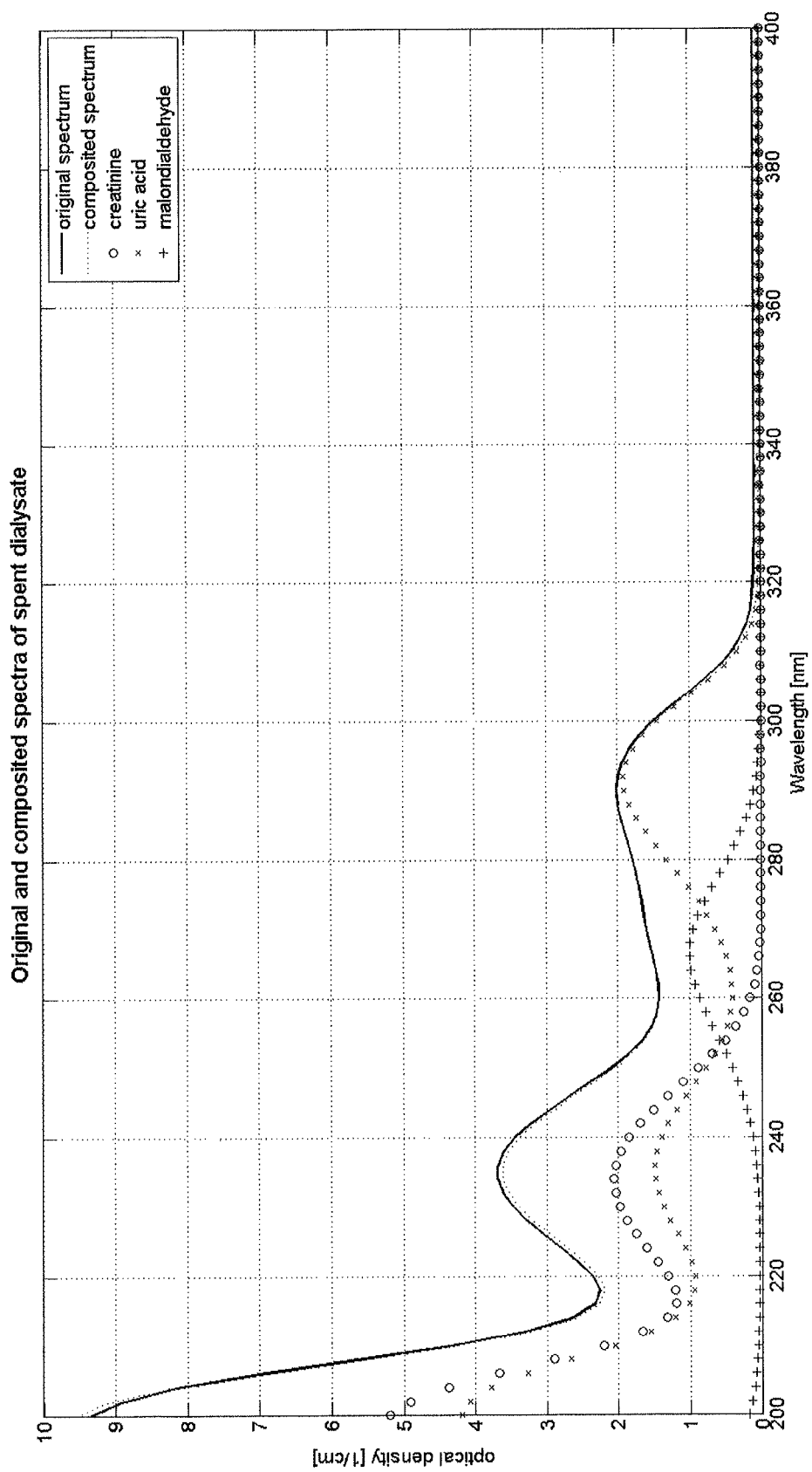
FIG. 5: Absorption behavior of uric acid, creatinine and malondialdehyde in spent dialysate in comparison to the individual substances.

Into a dialysate, 20 mg/l of uric acid, 30 mg/l creatinine and 10 mg/l malondialdehyde were added. The dialysate substituted with uric acid, creatinine and malondialdehyde was then measured spectrally (continuously, in 1 nm-steps from 200 nm to 400 nm). According to the apparatus of the invention an equation system with three unknowns are prepared at three wavelengths and the concentrations of uric acid, creatinine and malondialdehyde are calculated, wherein the accuracy was +/−10%. FIG. 5 shows the absorption behavior of uric acid, creatinine and malondialdehyde in spent dialysate and confirms the good applicability of the method though the reproduction of the spent dialysate from the linear combination of the mentioned substances.

The spectra shown are: —— spent dialysate, ●●● composited spectrum, ∘∘∘ creatinine, xxx uric acid and +++ malondialdehyde.

Example 6

The calculation of the concentrations of uric acid, malondialdehyde and creatinine was carried out for the samples from Example 5. The characteristic measuring points were selected according to the criteria mentioned in the section of selection criteria of a characteristic measuring point. The absorption has been measured at the wavelengths 235 nm, 266 nm and 290 nm; so the following equations are resulted:

$$A_{dialysate\ \lambda=290nm} = A_{\lambda=290nm\ uric\ acid} + A_{\lambda=290nm\ creatinine} + A_{\lambda=290nm\ malondialdehyde}$$

$$A_{dialysate\ \lambda=266nm} = A_{\lambda=266nm\ uric\ acid} + A_{\lambda=266nm\ creatinine} + A_{\lambda=266nm\ malondialdehyde}$$

$$A_{dialysate\ \lambda=235nm} = A_{\lambda=235nm\ uric\ acid} + A_{\lambda=235nm\ creatinine} + A_{\lambda=235nm\ malondialdehyde}$$

or with equation (1) and l=0.2 cm:

$$2.009 = 0.2\ \text{cm} \times (\epsilon_{290\ uric\ acid} \times c_{uric\ acid} + \epsilon_{290\ creatinine} \times c_{creatinine} + \epsilon_{290\ malondialdehyde} \times c_{matondialdehyde})$$

$$1.524 = 0.2\ \text{cm} \times (\epsilon_{266\ uric\ acid} \times c_{uric\ acid} + \epsilon_{266\ creatinine} \times c_{creatinine} + \epsilon_{266\ malondialdehyde} \times c_{matondialdehyde})$$

$$3.685 = 0.2\ \text{cm} \times (\epsilon_{235\ uric\ acid} \times c_{uric\ acid} + \epsilon_{235\ creatinine} \times c_{creatinine} + \epsilon_{235\ malondialdehyde} \times c_{matondialdehyde})$$

The extinction coefficient ε is substance- and wavelength-dependent, but is known for the substances to be determined. The length/is only a size of the measuring configuration. Thus, as unknowns and sizes to be determined are left the concentrations $c_{uric\ acid}$, $c_{creatinine}$ and $c_{malondialdehyde}$ by which the equation system (4b) was solved. The extinction coefficients ε were known or resulted from equation (1) of the substance spectra (see FIGS. 1 to 3) and are shown in table 4:

TABLE 4

Extinction coefficients

| wavelength | $\epsilon_{uric\ acid}$ | $\epsilon_{creatinine}$ | $\epsilon_{malondialdehyde}$ |
|---|---|---|---|
| 290 nm | 0.4344 l/(cm × mg) | 0.0012 l/(cm × mg) | 0.0510 l/(cm × mg) |
| 266 nm | 0.1114 l/(cm × mg) | 0.0060 l/(cm × mg) | 0.4868 l/(cm × mg) |
| 235 nm | 0.3416 l/(cm × mg) | 0.3809 l/(cm × mg) | 0.0319 l/(cm × mg) |

This equation system is solved, thus the concentrations are resulted as follows:

$c_{uric\ acid}$=21.8 mg/l, $c_{creatinine}$=27.9 mg/l and $c_{malonchaldehyde}$=10.3 mg/l.

The maximum deviation was here ca. 9%.

The equation system could be simplified, as already mentioned, (see table 5).

TABLE 5

Simplified representation of the extinction coefficients.

| wavelength | $\epsilon_{uric\ acid}$ | $\epsilon_{creatinine}$ | $\epsilon_{malondialdehyde}$ |
|---|---|---|---|
| 290 nm | 0.4344 l/(cm × mg) | 0 l/(cm × mg) | 0 l/(cm × mg) |
| 266 nm | 0.1114 l/(cm × mg) | 0 l/(cm × mg) | 0.4868 l/(cm × mg) |
| 235 nm | 0.3416 l/(cm × mg) | 0.3809 l/(cm × mg) | 0 l/(cm × mg) |

The concentrations are resulted in:

$c_{uric\ acid}$=21.8 mg/l, $c_{creatinine}$=27.9 mg/l and $c_{malondialdehyde}$=10.3 mg/l.

This simplification reduced substantially the computing effort while increasing the maximum error of ca. 16%.

The initial concentrations and the calculated concentrations are shown in table 6.

TABLE 6

Initial concentrations and calculated concentrations

|  | uric acid | creatinine | malondialdehyde |
|---|---|---|---|
| initial concentration | 20.0 mg/l | 30.0 mg/l | 10.0 mg/l |
| calculated concentration | 21.8 mg/l | 27.9 mg/l | 10.3 mg/l |
| deviation | +9% | −7% | +3% |

The wavelengths used in this calculation and substances are exemplary. It is understood by a person skilled in the art that any combination of the uremic toxins listed herein can be measured with the apparatus of the invention.

Example 7

Only a few of the more than 50 different uremic toxins in the spent dialysate actually show optical activity in the UV range. Uremic toxins with optical activity in the UV range comprise creatinine, uric acid, hippuric acid, indoxyl sulfate, 4-hydroxynonenal, malonaldehyde, p-cresol, phenol, retinol-binding protein and β2-microglobulin-fragments and/or combinations thereof. These uremic toxins differ in their optical properties, especially in their wavelength, mostly strong. In principle, it is therefore possible to determine the respective concentration from a mixture of several uremic toxins, as long as the spectra are sufficiently different and at least at as many wavelengths the absorption is determined, as UV active substances to be determined are present in the spent dialysate. In order to bring an additional security of the system and to increase the accuracy of the method, it can be measured even at more wavelengths, as there are substances, which dominate the absorption measurement. Such a system is called over-determined. In principle, it is useful to measure at points in the spectrum at which the absorption signal has specific features. Thus, for example, the characteristic wavelengths in the spent dialysate are 320 nm, 305 nm, 290 nm, 280 nm, 266 nm, 245 nm, 235 nm and 220 nm. However, other wavelengths are in principle possible. With the aforementioned wavelength combination, the concentration of up to eight optically active uremic toxins from the spent dialysate can be determined. If at the wavelengths λ=320 nm, λ=310, λ=305 nm, λ=300 nm, λ=290 nm, λ=280 nm, λ=270 nm, λ=266 nm, λ=260, λ=250 nm, λ=245 nm, λ=240 nm, λ=235 nm, λ=230 nm, λ=220 nm and λ=205 nm it should be measured, up to 16 substances can be determined. The characteristic measuring points must meet the criteria mentioned in the section of selection criteria for a characteristic measuring point. This amount of uremic toxins which differ in the spectrum partly strongly from each other and influence the absorption spectrum significantly is realistic in the dialysis. There are, of course, a plurality of other uremic toxins, which, however, have no effect on the irradiation with UV light, i.e. are not UV active and therefore do not interfere the UV measurements. In the dialysis, blood which is enriched with uremic toxins was purified in the dialyzer of the extracorporeal tube system. The toxins passed over into a wash solution in which they are diluted firstly by the different blood flow rates and dialysate flow rates and were finally rinsed. During disposing they passed through a tube segment, which was irradiated with ultraviolet light. According to each embodiment there is measured the absorption of the aqueous liquid for several wavelengths, for example 320 nm, 305 nm, 300 nm, 290 nm, 280 nm, 266 nm, 250 nm, 245 nm, 240 nm, 235 nm and 220 nm. The characteristic measuring points must meet the criteria mentioned in the section of selection criteria for a characteristic measuring point. Together with the substance constants deposited in the storage of the evaluation unit, which are wavelength-specific (cf. Table 1 and Example 1) an equation system of n equations and up to n unknowns can be established and solved, wherein n is the minimum number of the measuring points and the concentrations to be determined (cf. Example 1). In the present case, for the determination of 9 uremic toxins at 11 wavelengths are measured in order to solve the equation system even in the appearance of two redundant information.

A validation of the system was done by a simultaneous HPLC analysis. Usually the concentration of uremic toxins in the spent dialysate is less by a factor of 10 than in the blood. This has to do firstly with the dilution caused by blood flow and dialysate flow and is on the other hand also influenced from the purification performance of the dialyzer which is each according to the substance size typically <90%, each according to blood flow and dialyzer. Physiological parameters such as recirculation in the shunt of the dialysis patients reduce further the concentration of uremic toxins in the dialysate. Due to the high dilution, therefore, only the uremic toxins were detected by the measuring device, which have already a measurable optical activity in the undiluted state. The concentrations of the UV active uremic toxins in the blood plasma or blood serum known in the prior art are shown in table 7.

TABLE 7

Concentrations of the UV active uremic toxins.
Modified from Vanholder et al. (2003).

| UV active uremic toxin | normal concentration ($c_N$) | mean or median uremic concentration ($c_U$) | maximum concentration ($c_{MAX}$) |
|---|---|---|---|
| creatinine (mg/l) | <12.0 | 136.0 ± 46.0 | 240.0 |
| uric acid (mg/l) | <67.2 | 83.4 ± 44.5 | 146.7 |
| hippuric aicd (mg/l) | <5.0 | 247.0 ± 112.0 | 471.0 |
| indoxyl sulfate (mg/l) | 0.6 ± 5.4 | 53.0 ± 91.5 | 236.0 |
| malondialdehyde (µg/l) | 257.7 ± 81.7 | 428.8 ± 170.4 | 769.6 |
| p-cresol (mg/l) | 0.6 ± 1.0 | 20.1 ± 10.3 | 40.7 |
| phenol (mg/l) | 0.6 ± 0.2 | 2.7 ± 3.9 | 10.5 |
| retinol-binding protein (mg/l) | <80 | 192.0 ± 78.0 | 369.2 |
| $\beta_2$-microglobulin-fragments (mg/l) | <2.0 | 55.0 ± 7.9 | 100.0 |

If an equation system analogous to Example 6 is applied, at which the absorption is determined at at least 9 wavelengths (e.g. $\lambda$=320 nm, $\lambda$=305 nm, $\lambda$=290 nm, $\lambda$=280 nm, $\lambda$=266 nm, $\lambda$=250 nm, $\lambda$=240 nm, $\lambda$=230 nm and $\lambda$=220 nm), thus the equation system are solved in the avoidance of redundant information and the concentrations of the 9 uremic toxins are determined. In the present case, the absorption at the 11 wavelengths 320 nm, 305 nm, 300 nm, 290 nm, 280 nm, 266 nm, 250 nm, 245 nm, 240 nm, 235 nm and 220 nm was determined. After application of the equation system according to equation (1) (cf. also equation system in Example 6) the following values are resulted:

| substance | initial concentration | calculated concentration | deviation |
|---|---|---|---|
| creatinine | 80.3 mg/l | 75.7 mg/l | 5.7% |
| uric acid | 25.4 mg/l | 21.2 mg/l | 16.5% |
| hippuric acid | 90.9 mg/l | 83.7 mg/l | 7.9% |
| indoxyl sulfate | 15.4 mg/l | 12.5 mg/l | 18.8% |
| malondialdehyde | 255.3 µg/l | 250.0 µg/l | 2.1% |
| p-cresol | 5.1 mg/l | 5.8 mg/l | 13.7% |
| phenol | 0.6 mg/l | 0.8 mg/l | 33.3% |
| retinol-binding protein | 25.7 mg/l | 28.7 mg/l | 11.6% |
| $\beta_2$-microglobulin | 10.5 mg/l | 8.7 mg/l | 17.1% |

These measurements were carried out in the spent dialysate and are therefore, partly clearly under the concentrations of the blood concentration Example 8

Figure 6:
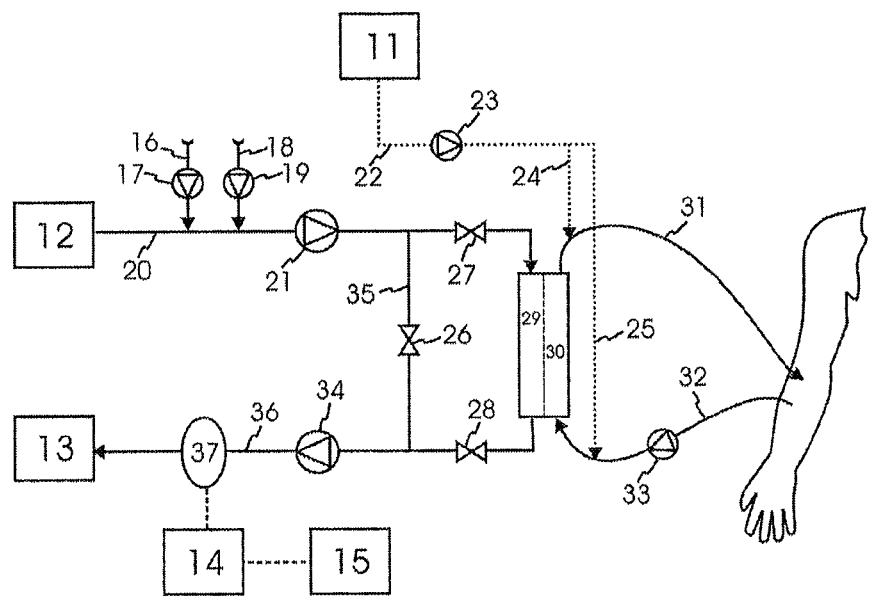
FIG. 6: Apparatus of the invention.

FIG. 6 shows a configuration of the dialysis apparatus with which the method of the invention is implemented. On the dialysate side there is at least one optical measuring device 37 which is also described herein as UV sensor. The blood of a patient is led from the patient into an extracorporeal circulation. The blood flows through a conduit 32 into the blood-side chamber 30 of a dialyzer and is returned through a conduit 31 to the patient. The flow rate of the blood circulation is controlled by a blood pump 33. The dialysis solution consists of a series of physiologically relevant substances which are dissolved in water, so that they are not withdrawn due to lack of the concentration gradient from the blood during the dialysis procedure. Therefore, the dialysis apparatus disclosed in FIG. 5 comprises a water inlet 12, two inlets 16 and 18 for concentrates of physiologically relevant substances which are dissolved in water, and two pumps 17 and 19. The water flow determines together with the concentrate flow or concentrate flows the composition of the dialysis solution. Via the dialysate circuit 20, the dialysis solution of the dialysis chamber 29 of the dialyzer, which is separated from the blood chamber 30 by a semipermeable membrane is fed. The dialysis solution is thereby fed from a pump 21 to the dialyzer. Another pump 34 sucks the dialysate and the ultrafiltrate removed from the blood. A bypass connection 35 is arranged between the pump 21 and 34. Also several valves 26, 27 and 28 are provided in order to control the dialysate flow. A conduit (outlet) 36 leads the spent dialysate to a UV sensor 37 with a radiation source 1 consisting of four light sources for substantially monochromatic electromagnetic radiation of the wavelengths $\lambda$=290 nm, $\lambda$=266 nm, $\lambda$=235 nm and $\lambda$=205 nm, which are controlled individually, which measures the absorption of the spent dialysate, wherein the UV sensor 37 is connected via an interface with a computer 14. The characteristic measuring points must meet the criteria mentioned in the section of selection criteria for a characteristic measuring point. The computer 14 processes the measured data. The result of the data processing is displayed on a device 15 and/or printed, wherein the device 15 is connected to the computer 14 via an interface. The conduit (outlet) 36 leads after the measurement with the UV sensor 37 the spent dialysate to the outflow system 13. The dotted lines 22, 24 and 25 represent an adaptation of the disclosed apparatus for treatments by means of hemodiafiltration. The replacement liquid is supplied from a replacement fluid source 11, flows through the tube 22 and is pumped by pump 23 into the blood inlet tube of the patient. In the case of a post-dilution hemodiafiltration the conduit 24 leads the replacement fluid to the venous conduit of the extracorporeal blood system. During a pre-dilution hemodiafiltration, both the conduit 24 and the conduit 25 can be used. The computer 14 controls all elements shown in FIG. 5 by means of appropriate interfaces, wherein the said interfaces are not depicted due to lack of clarity. The computer 14 collects information on other parameters of the dialysis apparatus, for example, blood flow, dialysate flow and/or treatment time. These parameters are processed together with the measured data.

The dialysis apparatus disclosed in this example is provided with further intended means, as they are commonly used for dialysis apparatuses. These further means are not disclosed, as they are not relevant for the implementation of the disclosed method of the invention.

The obtained Absorption curves are stored in a patient card, which is connected to the computer 14, or in a database, which is implemented in the computer 14. The number of the absorption curves to be saved and having been saved is variable and depends on the storage capacity of the medium. In a preferred embodiment of the last 20 treatments will be archived in an appropriate memory card. The stored treatment data will be overwritten by a First In-First Out process (FIFO). Additionally, a treatment to be determined by the user or by the attending physician can be defined as non-overwritable. In this case, the treatment data will be preserved until the treatment data are again defined as overwritable. The storage of the dialysis performance (Kt/V), or curves for the urea reduction rate (URR) is also possible.

Example 9

Figure 7:
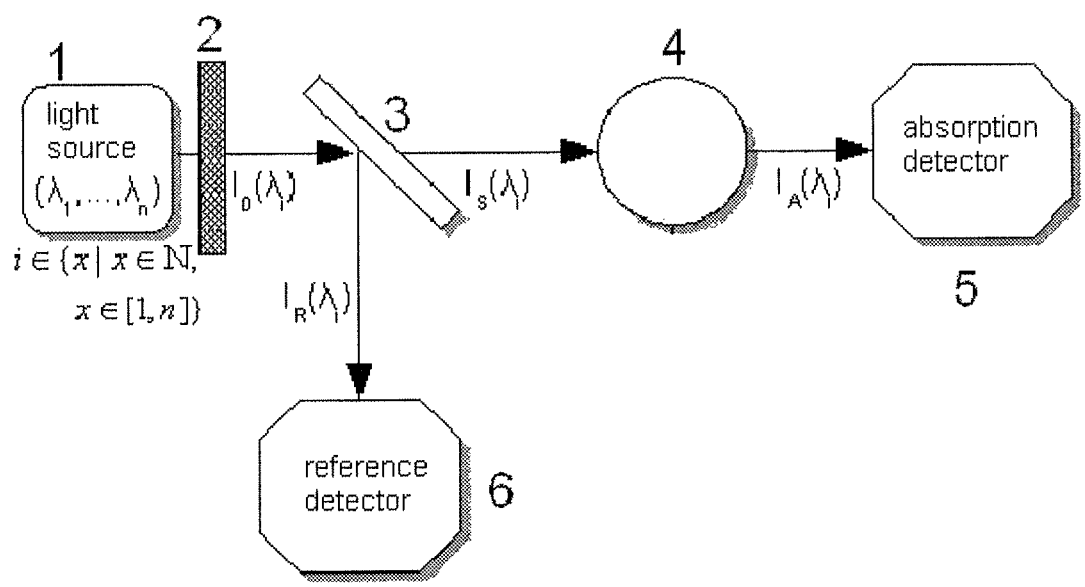
FIG. 7: Exemplary configuration of a sensor for the differentiation of different uremic toxins in the dialysate with a broad-band light source, a monochromator and a broad-band detector.
Figure 8:
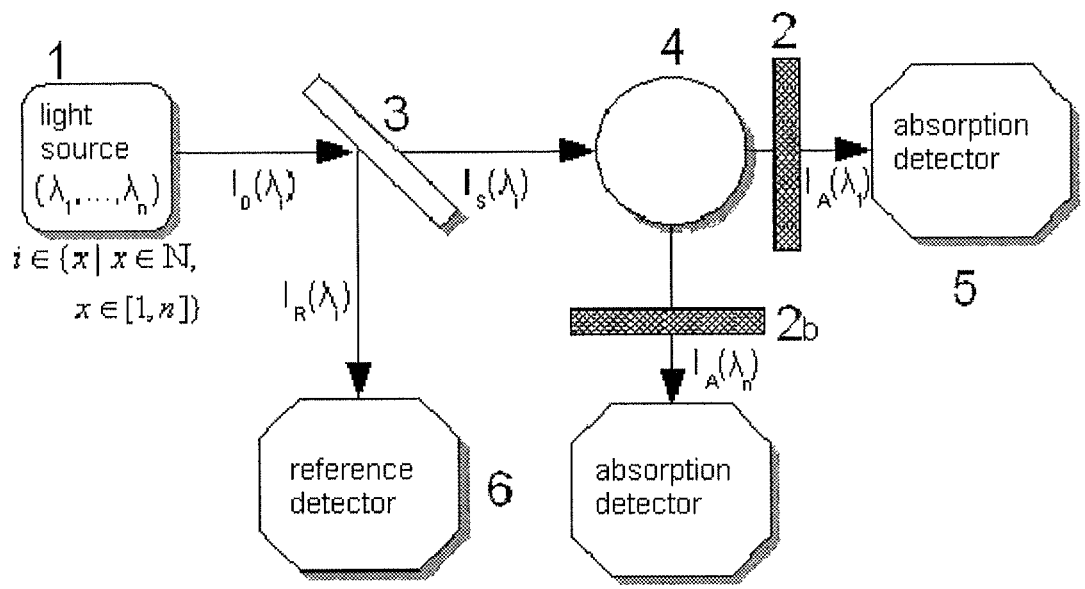
FIG. 8: Exemplary configuration of a sensor for the differentiation of different uremic toxins in the dialysate with a broad-band light source, several broad-band detector and several narrow-band filters which are designed differently, wherein dispensed with the monochromators if the detectors 1 to n are sufficiently narrow-banded.
Figure 9:
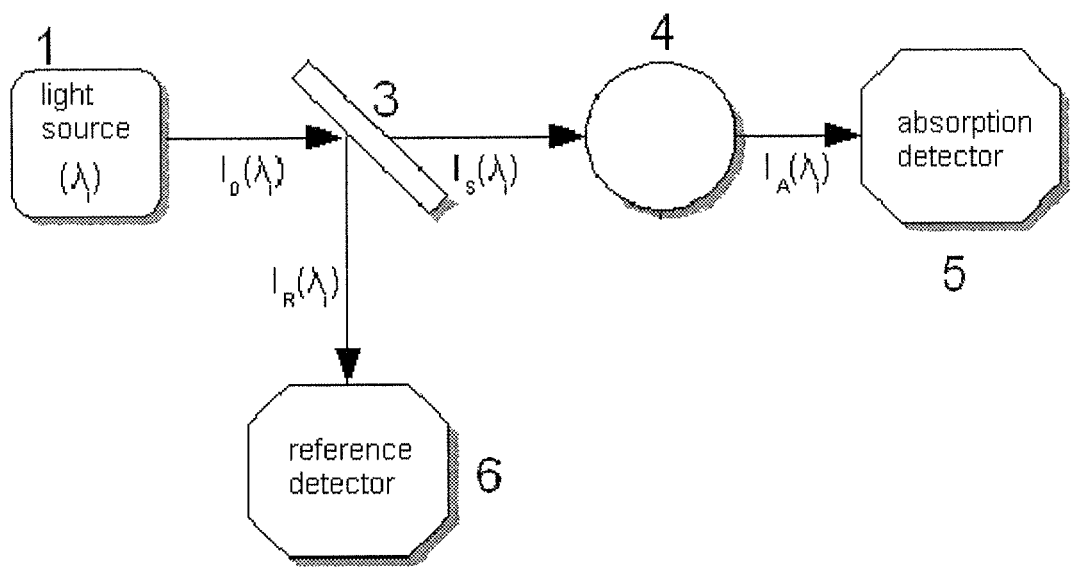
FIG. 9: Exemplary configuration of a sensor for the differentiation of different uremic toxins in the dialysate with a monochromatic light source and a detector. For the implementation of this invention n sensors of this embodiment with different monochromatic light sources serve for n wavelengths.

FIG. 7 shows an embodiment of the sensor configuration 37 for measuring the absorption at several wavelengths.

There, (1) represents a light source, which either consists of several (at least two) monochromatic wavelengths which are controlled individually, or is designed as a broad-band light source. In the last case, a wavelength-selective element (2) is necessary, which can be controlled in order to filter individual wavelengths. (3) represents a beam splitter (3) that splits the beam $I_0(\lambda_i)$ into two parts: $I_R(\lambda_i)$ and $I_S(\lambda)$. The proportion $I_R(\lambda_i)$ meets directly the reference detector (6), while the proportion of $I_S(\lambda_i)$ meets the sample to be examined (4). Depending on the absorption of the sample liquid, an intensity $I_A(\lambda_i)$ meets the absorption detector (5) which is smaller or equal to the original intensity $I_S(\lambda_i)$. The number of wavelengths n that could be used in the sensor, is in principle arbitrary, but should be at least two (at least i=[1,2]).

Example 10

A patient requiring dialysis was treated with an apparatus according to Example 7, wherein the sensor configuration was designed to measure the absorption according to Example 8. A dialysate sample of patients requiring dialysis was taken 10 minutes after the start of treatment and its absorption was determined spectrophotometrically at the wavelengths $\lambda=290$ nm, $\lambda=266$ nm and $\lambda=235$ nm. Subsequently, the concentrations of uric acid, creatinine, and malondialdehyde were calculated according to Example 6. The calculated concentrations were:

$c_{uric\ acid}=40.0$ mg/l, $c_{creatinine}=65.3$ mg/l and $c_{malondialdehyde}=250$ µg/l.

The characteristic measuring points were selected according to the criteria mentioned in the section of selection criteria for a characteristic measuring point.

The invention claimed is:

1. Apparatus for extracorporeal blood treatment with:
    a dialyzer which is separated by a semipermeable membrane into a first and second chamber, wherein the first chamber is arranged in a dialysate pathway and the second chamber is connectable to the blood circulation of a patient by means of a blood supply conduit and a blood return conduit,
    an inlet for fresh dialysate,
    an outlet for spent dialysate,
    a measuring device arranged in the outlet, wherein the measuring device has a radiation source for electromagnetic UV radiation,
    wherein the radiation source comprises either at least two monochromatic light sources or at least one polychromatic light source with monochromators for generating monochromatic UV radiation,
    a microprocessor unit, a storage unit as well as an output unit, wherein the measuring device is designed to generate substantially monochromatic electromagnetic UV-radiation of different wavelengths and to lead it through the outlet for spent dialysate, wherein at least one detector system is provided for the detection of the intensity or the absorption of the substantially monochromatic electromagnetic UV-radiation passing through the outlet for spent dialysate and in the storage unit a first equation system $$A_{\lambda i} = \sum_{j=1}^{n} A_j,$$

is deposited, wherein $A_{\lambda,i}$ is the total absorption of a mixture of substances at a predetermined wavelength $\lambda_i$, $\lambda_j$ is the absorption of a concerned substance within the mixture of substances, j is the concerned substance, and n is the number of the interesting components within the mixture of substances which contribute to the absorption, and
    wherein by means of the microprocessor unit with the aid of a reference absorption curve of a reference substance and a second equation system stored in the storage unit, the determination of at least one of absorption of the concerned substance or concentration of the concerned substance in the outlet is simplified with the second equation system $$A_{\lambda i}(dialysate) \approx \frac{A_{\lambda 1}(\text{reference substance})}{konst_i} + \sum_{j=2}^{n} \varepsilon_{j,\lambda_i} \cdot l \cdot c_j = \frac{A_{\lambda 1}(\text{reference substance})}{konst_i} + \sum_{j=2}^{n} A_j$$

wherein the reference substance absorbs at the wavelength $\lambda_i$ in spent dialysate almost entirely, wherein $c_i$ is the concentration of the concerned substance, and $konst_i$ is the ratio of absorption of a pure reference substance at the reference wavelength $\lambda_1$ to absorption of the pure reference substance at the wavelength $\lambda_i$.

2. Apparatus according to claim 1, wherein the radiation source consisting of several light sources is designed for the emission of electromagnetic radiation in the range of 180 nm to 380 nm.

3. Apparatus according to claim 1, wherein the radiation source has a plurality of light emitting diodes which are designed in each case for generating a substantially monochromatic electromagnetic UV radiation.

4. Apparatus according to claim 1, wherein the radiation source is designed for generating polychromatic electromagnetic radiation and for generating the substantially monochromatic electromagnetic radiation corresponding monochromators, including at least one of an optical filter which allows passage of only a specific wavelength or a band-pass filter with several pass ranges are provided.

5. Apparatus according to claim 1, wherein the microprocessor unit is designed to solve the equation system $$A_{\lambda i} = \sum_{j=1}^{n} A_j$$

using the equations $A_{\lambda_i}=\varepsilon_{j,\lambda_i} \cdot l \cdot c_j$ (1) and n measuring points and the absorption $A_1$ of a reference substance at a reference wavelength $\lambda_1$, wherein $A_j$ is the absorption of the substance j at a specific wavelength $\lambda_i$, $\varepsilon_{\lambda_i}$ is the wavelength-dependent extinction coefficient, l is the optical path length and $c_j$ is the respective concentration of the substance.

6. Apparatus according to claim 5, wherein the reference substance is selected from the group comprising the UV active uremic toxins creatinine, uric acid, hippuric acid, indoxyl sulfate, 4-hydroxynonenal, malondialdehyde, p-cresol, phenol, retinol-binding protein and β2microglobulin-fragments or combinations thereof.

7. Apparatus according to claim 1, wherein the reference substance is selected from the group comprising the UV active uremic toxins creatinine, uric acid, hippuric acid, indoxyl sulfate, 4-hydroxynonenal, malondialdehyde, p-cresol, phenol, retinol-binding protein and β2-microglobulin-fragments or combinations thereof.

8. Apparatus according to claim 6, wherein as reference substance uric acid is used.

9. Apparatus according to claim 1, wherein as reference substance uric acid is used.

10. Apparatus according to claim 5, wherein the reference wavelength $\lambda_1$ is in the range between 280 nm and 300 nm.

11. Apparatus according to claim 1, wherein the reference wavelength $\lambda_1$ is in the range between 280 nm and 300 nm.

12. Apparatus according to claim 1, wherein the radiation source is 10 monochromatic light sources.

13. Apparatus according to claim 1, wherein the detection of the intensity or the absorption is carried out at the wavelengths $\lambda=320$ nm, $\lambda=310$ nm, $\lambda=305$ nm, $\lambda=300$ nm, $\lambda=290$ nm, $\lambda=280$ nm, $\lambda=270$ nm, $\lambda=266$ nm, $\lambda=260$ nm, $\lambda=250$ nm, $\lambda=245$ nm, $\lambda=240$ nm, $\lambda=235$ nm, $\lambda=230$ nm, $\lambda=220$ nm and $\lambda=205$ nm.

* * * * *

UNITED STATES PATENT AND TRADEMARK OFFICE
CERTIFICATE OF CORRECTION

| | | |
|---|---|---|
| PATENT NO. | : 9,220,827 B2 | Page 1 of 1 |
| APPLICATION NO. | : 13/816968 | |
| DATED | : December 29, 2015 | |
| INVENTOR(S) | : Joern Meibaum et al. | |

It is certified that error appears in the above-identified patent and that said Letters Patent is hereby corrected as shown below:

In the claims:

Column 30, line 25 should read:

"$\lambda_i$ in spent dialysate almost entirely, wherein $c_j$ is the"

Signed and Sealed this
Eighth Day of March, 2016

Michelle K. Lee
*Director of the United States Patent and Trademark Office*